United States Patent
Chang et al.

(12)

(10) Patent No.: US 6,271,252 B1
(45) Date of Patent: Aug. 7, 2001

(54) CYCLIC AMINO ACID DERIVATIVES AS CELL ADHESION INHIBITORS

(75) Inventors: Linda Chang, Wayne; William K. Hagmann, Westfield; Malcolm MacCoss, Freehold, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/554,989

(22) PCT Filed: Nov. 23, 1998

(86) PCT No.: PCT/US98/25008

§ 371 Date: May 23, 2000

§ 102(e) Date: May 23, 2000

(87) PCT Pub. No.: WO99/26615

PCT Pub. Date: Jun. 3, 1999

(51) Int. Cl.[7] .......................... A61K 31/401; A61P 29/00; C07D 207/48; C07C 229/48
(52) U.S. Cl. .......................... 514/424; 514/415; 514/419; 514/422; 514/423; 514/428; 514/470; 548/492; 548/504; 548/507; 548/517; 548/537; 549/463
(58) Field of Search ........................... 514/424, 428, 514/470, 415; 548/492, 504, 507, 517, 537

(56) References Cited

U.S. PATENT DOCUMENTS 5,350,748 * 9/1994 Boschelli et al. ............... 514/273.2

* cited by examiner

*Primary Examiner*—Jane C. Oswecki
(74) *Attorney, Agent, or Firm*—Mollie M. Yang; David L. Rose

(57) ABSTRACT

Cyclic amino acid derivatives of Formula I are antagonists of VLA-4 and/or $\alpha_4\beta_7$, and as such are useful in the inhibition or prevention of cell adhesion and cell-adhesion mediated pathologies. These compounds may be formulated into pharmaceutical compositions and are suitable for use in the treatment of asthma, allergies, inflammation, multiple sclerosis, and other inflammatory and autoimmune disorders.

14 Claims, No Drawings

CYCLIC AMINO ACID DERIVATIVES AS CELL ADHESION INHIBITORS

This application is a 371 of PCT/US98/25008 filed Nov. 23, 1998.

BACKGROUND OF THE INVENTION

The present invention relates to novel substituted monocyclic and bicyclic amino acid derivatives which are useful for the inhibition and prevention of leukocyte adhesion and leukocyte adhesion-mediated pathologies. This invention also relates to compositions containing such compounds and methods of treatment using such compounds.

Many physiological processes require that cells come into close contact with other cells and/or extracellular matrix. Such adhesion events may be required for cell activation, migration, proliferation and differentiation. Cell-cell and cell-matrix interactions are mediated through several families of cell adhesion molecules (CAMs) including the selecting, integrins, cadherins and immunoglobulins. CAMs play an essential role in both normal and pathophysiological processes. Therefore, the targeting of specific and relevant CAMs in certain disease conditions without interfering with normal cellular functions is essential for an effective and safe therapeutic agent that inhibits cell-cell and cell-matrix interactions.

The integrin superfamily is made up of structurally and functionally related glycoproteins consisting of a and, heterodimeric, transmembrane receptor molecules found in various combinations on nearly every mammalian cell type. (for reviews see: E. C. Butcher, *Cell*, 67, 1033 (1991); T. A. Springer, *Cell*, 76, 301 (1994); D. Cox et al., "The Pharmacology of the Integrins." *Medicinal Research Rev.* 14, 195 (1994) and V. W. Engleman et al., "Cell Adhesion Integrins as Pharmaceutical Targets." in *Ann. Repts. in Medicinal Chemistry*, Vol. 31, J. A. Bristol, Ed.; Acad. Press, New York, 1996, p. 191).

VLA-4 ("very late antigen-4"; CD49d/CD29; or $\alpha_4\beta_1$) is an integrin expressed on all leukocytes, except platelets and mature neutrophils, including dendritic cells and macrophage-like cells and is a key mediator of the cell-cell and cell-matrix interactions of these cell types (see M. E. Hemler, "VLA Proteins in the Integrin Family: Structures, Functions, and Their Role on Leukocytes." *Ann. Rev. Immunol.* 8, 365 (1990)). The ligands for VLA-4 include vascular cell adhesion molecule-1 (VCAM-1) and the CS-1 domain of fibronectin (FN). VCAM-1 is a member of the Ig superfamily and is expressed in vivo on endothelial cells at sites of inflammation. (See R. Lobb et al. "Vascular Cell Adhesion Molecule 1." in Cellular and Molecular Mechanisms of Inflammation, C. G. Cochrane and M. A. Gimbrone, Eds.; Acad. Press, San Diego, 1993, p. 151.) VCAM-1 is produced by vascular endothelial cells in response to pro-inflammatory cytokines (See A. J. H. Gearing and W. Newman, "Circulating adhesion molecules in disease.", *Immunol. Today*, 14, 506 (1993). The CS-1 domain is a 25 amino acid sequence that arises by alternative splicing within a region of fibronectin. (For a review, see R. O. Hynes "Fibronectins.", Springer-Velag, New York, 1990.) A role for VLA-4/CS-1 interactions in inflammatory conditions has been proposed (see M. J. Elices, "The integrin $\alpha_4\beta_1$ (VLA-4) as a therapeutic target" in *Cell Adhesion and Human Disease*, Ciba Found. Symp., John Wiley & Sons, New York, 1995, p. 79).

$\alpha_4\beta_7$ (also referred to as LPAM-1 and $\alpha_4\beta_p$) is an integrin expressed on leukocytes and is a key mediator of leukocyte trafficking and homing in the gastrointestinal tract (see C. M. Parker et al., *Proc. Natl. Acad. Sci. USA*, 89, 1924 (1992)). The ligands for $\alpha_4\beta_7$ include mucosal addressing cell adhesion molecule-1 (MadCAM-1) and, upon activation of $\alpha_4\beta_7$, VCAM-1 and fibronectin (Fn). MadCAM-1 is a member of the Ig superfamily and is expressed in vivo on endothelial cells of gut-associated mucosal tissues of the small and large intestine ("Peyer's Patches") and lactating mammary glands. (See M. J. Briskin et al., *Nature*, 363, 461 (1993); A. Hamann et al., *J. Immunol.*, 152, 3282 (1994)). MadCAM-1 can be induced in vitro by proinflammatory stimuli (See E. E. Sikorski et al. *J. Immunol.*, 151, 5239 (1993)). MadCAM-1 is selectively expressed at sites of lymphocyte extravasation and specifically binds to the integrin, $\alpha_4\beta_7$.

Neutralizing anti-$\alpha_4$ antibodies or blocking peptides that inhibit the interaction between VLA-4 and/or $\alpha_4\beta_7$ and their ligands have proven efficacious both prophylactically and therapeutically in several animal models of disease, including i) experimental allergic encephalomyelitis, a model of neuronal demyelination resembling multiple sclerosis (for example, see T. Yednock et al., "Prevention of experimental autoimmune encephalomyelitis by antibodies against $\alpha_4\beta_1$ integrin." *Nature*, 356, 63 (1993) and E. Keszthelyi et al., "Evidence for a prolonged role of $\alpha_4$ integrin throughout active experimental allergic encephalomyelitis." *Neurology*, 47, 1053 (1996)); ii) bronchial hyperresponsiveness in sheep and guinea pigs as models for the various phases of asthma (for example, see W. M. Abraham et al., "$\alpha_4$-Integrins mediate antigen-induced late bronchial responses and prolonged airway hyperresponsiveness in sheep." *J. Clin. Invest.* 93, 776 (1993) and A. A. Y. Milne and P. P. Piper, "Role of VLA-4 integrin in leukocyte recruitment and bronchial hyperresponsiveness in the Guinea-pig." *Eur. J. Pharmacol.*, 282, 243 (1995)); iii) adjuvant-induced arthritis in rats as a model of inflammatory arthritis (see C. Barbadillo et al., "Anti-VLA-4 mAb prevents adjuvant arthritis in Lewis rats." *Arthr. Rheuma.* (Suppl.), 36 95 (1993) and D. Seiffge, "Protective effects of monoclonal antibody to VLA-4 on leukocyte adhesion and course of disease in adjuvant arthritis in rats." *J. Rheumatol.*, 23, 12 (1996)); iv) adoptive autoimmune diabetes in the NOD mouse (see J. L. Baron et al., "The pathogenesis of adoptive murine autoimmune diabetes requires an interaction between $\alpha_4$-integrins and vascular cell adhesion molecule-1.", *J. Clin. Invest.*, 93, 1700 (1994), A. Jakubowski et al., "Vascular cell adhesion molecule-Ig fusion protein selectively targets activated α4-integrin receptors in vivo: Inhibition of autoimmune diabetes in an adoptive transfer model in nonobese diabetic mice." *J. Immunol.*, 155, 938 (1995), and X. D. Yang et al., "Involvement of beta 7 integrin and mucosal address in cell adhesion molecule-1 (MadCAM-1) in the development of diabetes in nonobese diabetic mice", Diabetes, 46, 1542 (1997)); v) cardiac allograft survival in mice as a model of organ transplantation (see M. Isobe et al., "Effect of anti-VCAM-1 and anti-VLA- 4 monoclonal antibodies on cardiac allograft survival and response to soluble antigens in mice.", *Transplant. Proc.*, 26, 867 (1994) and S. Molossi et al., "Blockade of very late antigen-4 integrin binding to fibronectin with connecting segment-1 peptide reduces accelerated coronary arteripathy in rabbit cardiac allografts."*J. Clin Invest.*, 95, 2601 (1995)); vi) spontaneous chronic colitis in cotton-top tamarins which resembles human ulcerative colitis, a form of inflammatory bowel disease (see D. K. Podoisky et al., "Attenuation of colitis in the Cotton-top tamarin by anti-$\alpha_4$ integrin monoclonal antibody.", *J. Clin. Invest.*, 92, 372 (1993)); vii) contact hypersensitivity models as a model for skin allergic reactions (see T. A. Ferguson and T. S. Kupper, "Antigen-independent processes in antigen-specific immunity.", *J. Immunol.*, 150, 1172 (1993) and P. L. Chisholm et al., "Monoclonal antibodies to the integrin α-4 subunit inhibit the murine contact hypersensitivity response." *Eur. J. Immunol.*, 23, 682 (1993)); viii) acute neurotoxic nephritis (see M. S. Mulligan et al., "Requirements for leukocyte adhesion molecules in nephrotoxic nephritis.", *J. Clin. Invest.*, 91, 577 (1993)); ix) tumor metastasis (for examples, see M. Edward, "Integrins and other adhesion molecules involved in melanocytic tumor progression.", *Curr. Opin. Oncol.*, 7, 185 (1995)); x) experimental autoimmune thyroiditis (see R. W. McMurray et al., "The role of α4 integrin and intercellular adhesion molecule-1 (ICAM-1) in murine experimental autoimmune thyroiditis." *Autoimmunity*, 23, 9 (1996); xi) ischemic tissue damage following arterial occlusion in rats (see F. Squadrito et al., "Leukocyte integrin very late antigen-4/vascular cell adhesion molecule-1 adhesion pathway in splanchnic artery occlusion shock." *Eur. J. Pharmacol.*, 318, 153 (1996); and xii) inhibition of TH2 T-cell cytokine production including IL-4 and IL-5 by VLA-4 antibodies which would attenuate allergic responses (J. Clinical Investigation 100, 3083 (1997). The primary mechanism of action of such antibodies appears to be the inhibition of lymphocyte and monocyte interactions with CAMs associated with components of the extracellular matrix, thereby limiting leukocyte migration to extravascular sites of injury or inflammation and/or limiting the priming and/or activation of leukocytes.

There is additional evidence supporting a possible role for VLA-4 interactions in other diseases, including rheumatoid arthritis; various melanomas, carcinomas, and sarcomas; inflammatory lung disorders; acute respiratory distress syndrome (ARDS); atherosclerotic plaque formation; restenosis; uveitis and circulatory shock (for examples, see A. A. Postigo et al., "The $\alpha_4\beta_1$/VCAM-1 adhesion pathway in physiology and disease.", *Res. Immunol.*, 144, 723 (1994) and J.-X. Gao and A. C. Issekutz, "Expression of VCAM-1 and VLA-4 dependent T-lymphocyte adhesion to dermal fibroblasts stimulated with proinflammatory cytokines." *Immunol.* 89,375 (1996)).

At present, there is a humanized monoclonal antibody (Antegren® Athena Neurosciences/Elan ) against VLA-4 in clinical development for the treatment of "flares" associated with multiple sclerosis and a humanized monoclonal antibody (ACT-1®/LDP-02 LeukoSite) against $\alpha_4\beta_7$ in clinical development for the treatment of inflammatory bowel disease. Several peptidyl antagonists of VLA-4 have been described (D. Y. Jackson et al., "Potent α4β1 peptide antagonists as potential anti-inflammatory agents", *J. Med. Chem.*, 40, 3359 (1997); H. N. Shroff et al., "Small peptide inhibitors of α4β7 mediated MadCAM-1 adhesion to lymphocytes", *Bioorg. Med. Chem. Lett.*, 6, 2495 (1996); U.S. Pat. No. 5,510,332, WO97/03094, WO97/02289, WO96/40781, WO96/22966, WO96/20216, WO96/01644, WO96/06108, WO95/15973). There is one report of non-peptidyl inhibitors of the ligands for α4-integrins (WO96/31206). There still remains a need for low molecular weight, specific inhibitors of VLA-4- and α4β7-dependent cell adhesion that have improved pharmacokinetic and pharmacodynamic properties such as oral bioavailability and significant duration of action. Such compounds would prove to be useful for the treatment, prevention or suppression of various pathologies mediated by VLA-4 and α4β7 binding and cell adhesion and activation.

SUMMARY OF THE INVENTION

The compounds of the present invention are antagonists of the VLA-4 integrin ("very late antigen-4"; CD49d/CD29; or $\alpha_4\beta_1$) and/or the α4β7 integrin (LPAM-1 and $\alpha_4\beta_p$), thereby blocking the binding of VLA-4 to its various ligands, such as VCAM-1 and regions of fibronectin and/or α4β7 to its various ligands, such as MadCAM-1, VCAM-1 and fibronectin. Thus, these antagonists are useful in inhibiting cell adhesion processes including cell activation, migration, proliferation and differentiation. These antagonists are useful in the treatment, prevention and suppression of diseases mediated by VLA-4 and/or α4β7 binding and cell adhesion and activation, such as multiple sclerosis, asthma, allergic rhinitis, allergic conjunctivitis, inflammatory lung diseases, rheumatoid arthritis, septic arthritis, type I diabetes, organ transplantation, restenosis, autologous bone marrow transplantation, inflammatory sequelae of viral infections, myocarditis, inflammatory bowel disease including ulcerative colitis and Crohn's disease, certain types of toxic and immune-based nephritis, contact dermal hypersensitivity, psoriasis, tumor metastasis, and atherosclerosis.

DETAILED DESCRIPTION OF THE INVENTION

The present invention provides novel compounds of Formula I

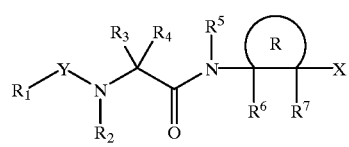

or a pharmaceutically acceptable salt thereof wherein:

X is
1) —C(O)OR$^d$,
2) —P(O)(OR$^d$)(OR$^e$)
3) —P(O)(R$^d$)(OR$^e$)
4) —S(O)$_m$OR$^d$,
5) —S(O)$_m$NR$^d$R$^h$;
6) —C(O)NR$^d$R$^h$, or
7) -5-tetrazolyl;

Y is
1) —C(O)—,
2) —O—C(O)—,
3) —NR$^d$R$^e$—C(O)—,
4) —S(O)$_2$—,
5) —P(O)(OR$^4$) or
6) C(O)C(O);

R is
a saturated or partially saturated monocyclic or bicyclic ring having 0–4 heteroatoms selected from N, O and S, optionally benzo-fused and optionally substituted with from 1–4 groups selected from R$^b$;

R$^1$
is 1) C$_{1-10}$alkyl,
2) C$_{2-10}$alkenyl,
3) C$_{2-10}$alkynyl,
4) Cy,
5) Cy-C$_{1-10}$alkyl,
6) Cy-C$_{2-10}$alkenyl,
7) Cy-C$_{2-10}$alkynyl, wherein alkyl, alkenyl, and alkynyl are optionally substituted with one to four substituents independently selected from R$^a$; and Cy is optionally substituted with one to four substituents independently selected from R$^b$;

$R^2$ and $R^3$ are independently
1) hydrogen, or
2) a group selected from $R^1$; or
$R^2$ and $R^3$ together with the atoms to which they are attached form a ring of 4 to 7 members containing 0–2 additional heteroatoms independently selected from oxygen, sulfur and nitrogen, wherein said ring may be isolated or benzo-fused, and optionally substituted with one to four substituents independently selected from $R^b$;

$R^4$ is
1) hydrogen,
2) $C_{1-10}$alkyl,
3) $C_{2-10}$alkenyl,
4) $C_{2-10}$alkynyl,
5) aryl,
6) aryl $C_{1-10}$alkyl,
7) heteroaryl, or
8) heteroaryl $C_{1-10}$alkyl, wherein alkyl, alkenyl and alkynyl are optionally substituted with one to four substituents independently selected from $R^a$, and aryl and heteroaryl are optionally substituted with one to four substituents independently selected from $R^b$; or $R^3$, $R^4$ and the carbon to which they are attached form a 3–7 membered ring optionally containing 1–2 heteroatoms selected from N, O and S;

$R^5$ is
1) hydrogen,
2) $C_{1-10}$ alkyl,
3) Cy, or
4) Cy-$C_{1-10}$ alkyl, wherein alkyl is optionally substituted with one to four substituents independently selected from $R^a$; and Cy is optionally substituted with one to four substituents independently selected from $R^b$;

$R^6$ is selected from the group consisting of:
1) hydrogen,
2) $C_{1-10}$alkyl,
3) $C_{2-10}$alkenyl,
4) $C_{2-10}$alkynyl,
5) Cy-$(Cy^1)_p$,
6) Cy-$(Cy^1)_p$-$C_{1-10}$alkyl,
7) Cy-$(Cy^1)_p$-$C_{2-10}$alkenyl,
8) Cy-$(Cy^1)_p$-$C_{2-10}$alkynyl, alkyl, alkenyl and alkynyl are optionally substituted with one to four substituents independently selected from $R^a$; and Cy and $Cy^1$ are optionally substituted with one to four substituents independently selected from $R^b$; or $R^6$ together with the carbon atom to which it is attached and another carbon atom of R form a ring having from 5–8 members optionally substituted with $R^b$;

$R^7$ is
1) hydrogen
2) $C_{1-10}$alkyl,
3) $C_{2-10}$alkenyl,
4) $C_{2-10}$alkynyl,
5) Cy,
6) Cy-$C_{1-10}$alkyl,
7) Cy-$C_{2-10}$alkenyl,
8) Cy-$C_{2-10}$alkynyl,
9) $C_{1-10}$alkoxy,
10) Cy-O,
11) Cy-$C_{1-10}$alkoxy,
12) —$S(O)_m R^d$,
13) —$SR^d$,
14) —$S(O)_2 OR^d$,
15) —$S(O)_m NR^d R^e$,
16) hydroxy,
17) —$NR^d R^e$,
18) —$O(CR^f R^g)_n NR^d R^e$,
19) —$OC(O)R^d$,
20) —CN,
21) —$C(O)NR^d R^e$,
22) —$NR^d C(O)R^e$,
23) —$OC(O)NR^d R^e$,
24) —$NR^d C(O)OR^e$, or
25) —$NR^d C(O)NR^d R^e$, wherein alkyl, alkenyl and alkynyl are optionally substituted with one to four substituents selected from $R^a$, and Cy is optionally substituted with one to four substituents independently selected from $R^b$; or $R^7$ together with the carbon atom to which it is attached and another carbon atom of R form a ring having from 5–8 members optionally substituted with $R^b$; or $R^6$ and $R^7$ together represents a double bond between the carbon atoms to which they are attached;

$R^a$ is
1) —$CF_3$;
2) —$OR^d$,
3) —$NO_2$,
4) halogen
5) —$S(O)_m R^d$,
6) —$SR^d$,
7) —$S(O)_2 OR^d$,
8) —$S(O)_m NR^d R^e$,
9) —$NR^d R^e$,
10) —$O(CR^f R^g)_n NR^d R^e$,
11) —$C(O)R^d$,
12) —$CO_2 R^d$,
13) —$CO_2(CR^f R^g)_n CONR^d R^e$,
14) —$OC(O)R^d$,
15) —CN,
16) —$C(O)NR^d R^e$,
17) —$NR^d C(O)R^e$,
18) —$OC(O)NR^d R^e$,
19) —$NR^d C(O)OR^e$, or
20) —$NR^d C(O)NR^d R^e$;
21) —$CR^d(N—OR^e)$, or
22) Cy optionally substituted with a group independently selected from $R^c$;

$R^b$ is
1) a group selected from $R^a$,
2) $C_{1-10}$ alkyl,
3) $C_{2-10}$ alkenyl,
4) $C_{2-10}$ alkynyl, or
5) Cy-$C_{1-10}$ alkyl, wherein alkyl, alkenyl, alkynyl, and Cy are optionally substituted with a group independently selected from $R^c$;

$R^c$ is
1) halogen,
2) amino,
3) carboxy,
4) $C_{1-4}$alkyl,
5) $C_{1-4}$alkoxy,
6) aryl,
7) aryl $C_{1-4}$alkyl, or
8) aryloxy;

$R^d$ and $R^e$ are independently selected from hydrogen, $C_{1-10}$alkyl, $C_{2-10}$alkenyl, $C_{2-10}$alkynyl, Cy and Cy-$C_{1-10}$alkyl, wherein alkyl, alkenyl, alkynyl and Cy is optionally substituted with one to four substituents independently selected from $R^c$; or $R^d$ and $R^e$ together with the atoms to which they are attached form a heterocyclic ring of 5 to 7 members containing 0–2 additional heteroatoms independently selected from oxygen, sulfur and nitrogen;

$R^f$ and $R^g$ are independently selected from hydrogen, $C_{1-10}$alkyl, Cy and Cy-$C_{1-10}$alkyl; or $R^f$ and $R^g$ together with the carbon to which they are attached form a ring of 5 to 7 members containing 0–2 heteroatoms independently selected from oxygen, sulfur and nitrogen;

Rh is
1) hydrogen,
2) $C_{1-10}$alkyl,
3) $C_{2-10}$alkenyl,
4) $C_{2-10}$alkynyl,
5) cyano,
6) aryl,
7) aryl $C_{1-10}$alkyl,
8) heteroaryl,
9) heteroaryl $C_{1-10}$alkyl, or
10) —$SO_2R^i$;

wherein alkyl, alkenyl, and alkynyl are optionally substituted with one to four substituents independently selected from $R^a$; and aryl and heteroaryl are each optionally substituted with one to four substituents independently selected from $R^b$;

$R^i$
1) $C_{1-10}$alkyl,
2) $C_{2-10}$alkenyl,
3) $C_{2-10}$alkynyl, or
4) aryl;

wherein alkyl, alkenyl, alkynyl and aryl are each optionally substituted with one to four substituents independently selected from $R^c$;

Cy and $Cy^1$ are independently
1) cycloalkyl,
2) heterocyclyl,
3) aryl, or
4) heteroaryl;

m is 0, 1 or 2;

n is an integer from 1 to 10;

p is 0 or 1.

In one subset of compounds of formula I $R^2$, $R^3$ and the atoms to which they are attached together form a ring selected from pyrrolidine, tetrahydroisoquinoline, piperidine, and thiazolidine each of which is optionally substituted with from one to four groups selected from $R^b$. Preferred rings are pyrrolidine and tetrahydroisoquinoline optionally substituted with one or two groups selected from $R^b$.

In another subset of compounds of formula I $R^2$ is hydrogen, $C_{1-10}$alkyl, Cy or Cy-$C_{1-10}$alkyl, wherein alkyl is optionally substituted with from one to four groups selected from $R^a$ and Cy is optionally substituted with from one to four groups selected from $R^b$.

In one subset of compounds of formula I $R^1$ is Cy or Cy-$C_{1-10}$alkyl where Cy and alkyl are optionally substituted as provided above under formula I. For the purpose of $R^1$, Cy is preferably aryl optionally substituted with one or two groups selected from $R^b$.

In another subset of compounds of formula I Y is —C(O)— or $SO_2$. Preferably Y is $SO_2$.

In another subset of compounds of formula I X is —C(O)O$R^d$.

In another subset of compounds of formula I R, $R^6$ and $R^7$ together represent the following (N and X are shown as necessary):

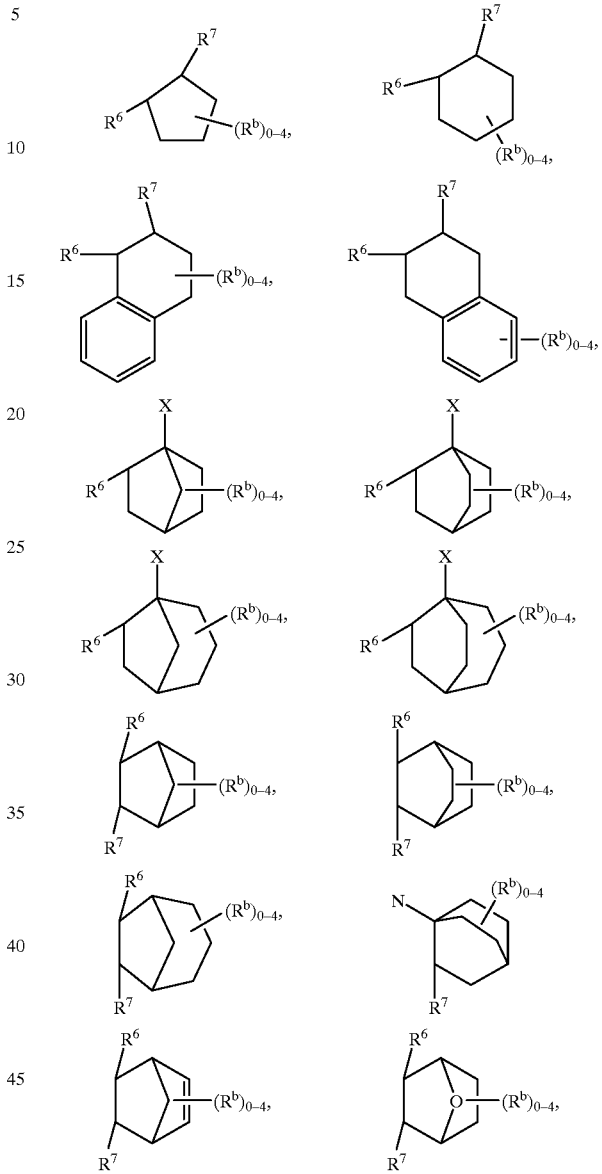

Representative compounds of Formula I include:
3-exo-[N-(N-3,5-dichlorobenzenesulfonyl)-(L)-prolyl]amino-bicyclo[2.2.1]-heptane-2-carboxylic acid;
cis-2-[N-(N-3,5-dichlorobenzenesulfonyl)-(L)-prolyl]amino-1-cyclohexanecarboxylic acid;
trans-2-[N-(N-3,5-dichlorobenzenesulfonyl)-(L)-prolyl]amino-1-cyclohexanecarboxylic acid;
cis-2-[N-(N-3,5-dichlorobenzenesulfonyl)-(L)-prolyl]amino-1-cyclopentanecarboxylic acid;
2-[N-(N-3,5-dichlorobenzenesulfonyl)-(L)-prolyl]amino-1-cyclopentene-1-carboxylic acid;
3-endo-[N-(N-3,5-dichlorobenzenesulfonyl)-(L)-prolyl]amino-bicyclo[2.2.1]-hept-5-ene-2-carboxylic acid;
3-endo-[N-(N-3,5-dichlorobenzenesulfonyl)-(L)-prolyl]-amino-bicyclo[2.2.1]-heptane-2-carboxylic acid;
trans-2-[N-(N-3,5-dichlorobenzenesulfonyl-N-methyl)-(L)-valyl]-amino-1-cyclohexanecarboxylic acid;
trans-2-[N-(N-cyclohexyl-N-3,5-dichlorobenzenesulfonyl)glycyl]-amino-1-cyclohexanecarboxylic acid;

trans-2-[N-(N-3,5-dichlorobenzenesulfonyl-N-methyl)-(L)-phenylalanyl]amino-1-cyclohexanecarboxylic acid;
trans-2-[N-(N-3,5-dichlorobenzenesulfonyl)-(L)-phenylalanyl]-amino-1-cyclohexanecarboxylic acid;
3-endo-[N-(N-3,5-dichlorobenzenesulfonyl)-(L)-prolyl] amino-bicyclo[2.2.2]-octane-2-carboxylic acid;
3-endo-[N-(N-3,5-dichlorobenzenesulfonyl)-(L)-2(S)-methyl-prolyl]amino-bicyclo[2.2.1]-heptane-2-carboxylic acid;
3-exo-[N-(N-3,5-dichlorobenzenesulfonyl)-(L)-prolyl] amino-7-oxobicyclo[2.2.1]-heptane-2-carboxylic acid;
3-endo-[N-(N-3,5-dichlorobenzenesulfonyl)-(L)-prolyl] amino-7-oxobicyclo[2.2.1]-heptane-2-carboxylic acid.

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. The term also includes monocyclic ring fused to an aryl group in which the point of attachment is on the non-aromatic portion. Examples of cycloalkyl include cyclopropyl, cyclopentyl, cyclohexyl, cycloheptyl, tetrahydronaphthyl, decahydronaphthyl, indanyl, and the like.

"Aryl" means mono- or bicyclic aromatic rings containing only carbon atoms. The term also includes aryl group fused to a monocyclic cycloalkyl or monocyclic heterocyclyl group in which the point of attachment is on the aromatic portion. Examples of aryl include phenyl, naphthyl, indanyl, indenyl, tetrahydronaphthyl, 2,3-dihydrobenzofuranyl, benzopyranyl, 1,4-benzodioxanyl, and the like.

"Heteroaryl" means a mono- or bicyclic aromatic ring containing at least one heteroatom selected from N, O and S, with each ring containing 5 to 6 atoms. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms. The term also includes monocyclic heterocycle fused to an aryl or heteroaryl group in which the point of attachment is on the non-aromatic portion. Examples of "heterocyclyl" include pyrrolidinyl, piperidinyl, piperazinyl, imidazolidinyl, 2,3-dihydrofuro(2,3-b)pyridyl, benzoxazinyl, tetrahydrohydroquinolinyl, tetrahydroisoquinolinyl, dihydroindolyl, and the like.

"Halogen" includes fluorine, chlorine, bromine and iodine.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The ability of the compounds of Formula I to antagonize the actions of VLA-4 and/or α4β7 integrin makes them useful for preventing or reversing the symptoms, disorders or diseases induced by the binding of VLA-4 and or α4β7 to their various respective ligands. Thus, these antagonists will inhibit cell adhesion processes including cell activation, migration, proliferation and differentiation. Accordingly, another aspect of the present invention provides a method for the treatment (including prevention, alleviation, amelioration or suppression) of diseases or disorders or symptoms mediated by VLA-4 and/or α4β7 binding and cell adhesion and activation, which comprises administering to a mammal an effective amount of a compound of Formula I. Such diseases, disorders, conditions or symptoms are for example (1) multiple sclerosis, (2) asthma, (3) allergic rhinitis, (4) allergic conjunctivitis, (5) inflammatory lung diseases, (6) rheumatoid arthritis, (7) septic arthritis, (8) type I diabetes, (9) organ transplantation rejection, (10) restenosis, (11) autologous bone marrow transplantation, (12) inflammatory sequelae of viral infections, (13) myocarditis, (14) inflammatory bowel disease including ulcerative colitis and Crohn's disease, (15) certain types of toxic and immune-based nephritis, (16) contact dermal hypersensitivity, (17) psoriasis, (18) tumor metastasis, (19) hepatitis, and (20) atherosclerosis.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3.536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/mL |
| --- | --- |
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |
| Tablet | mg/tablet |
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |
| Capsule | mg/capsule |
| Compound of Formula I | 25 |
| Lactose Powder | 573.5 |
| Magnesium Stearate | 1.5 |
| | 600 |
| Aerosol | Per canister |
| Compound of Formula I | 24 mg |
| Lecithin, NF Liquid Concentrate | 1.2 mg |
| Trichlorofluoromethane, NF | 4.025 g |
| Dichlorodifluoromethane, NF | 12.15 g |

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (a) other VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxicam), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors such as celecoxib; (h) inhibitors of phosphodiesterase type IV (PDE-IV); (i) antagonists of the chemokine receptors, especially CCR-1, CCR-2, and CCR-3; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone, pioglitazone, englitazone, MCC-555, BRL49653 and the like); (l) preparations of interferon beta (interferon beta-1a, interferon beta-1b); (m) anticholinergic agents such as muscarinic antagonists (ipratropium bromide); (n) other compounds such as 5-aminosalicylic acid and prodrugs thereof, antimetabolites such as azathioprine and 6-mercaptopurine, and cytotoxic cancer chemotherapeutic agents.

The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The compounds of Formula I may be prepared by several general synthetic methods as described in for example, *Principles of Peptide Synthesis*, 2nd Ed., M. Bodanszky, Springer Verlag, Berlin Heidelberg, 1993; W. Oppolzer in *Comprehensive Organic Synthesis*, B. M. Trost & I. Fleming, Eds., Pergamon Press, Oxford, 1991, Vol. 5, p 315; R. F. Heck, in *Comprehensive Organic Synthesis*, B. M. Trost & I. Fleming, Eds., Pergamon Press, Oxford, 1991, Vol. 4, p 833; A. de Maijere, F. E. Meyer, *Angew. Chem. Int. Ed. Engl.*, 33, 1994, 2379–2411. The compound of the present invention can be prepared by procedures illustrated in the accompanying schemes.

Although the Reaction Schemes described below are reasonably general, it will be understood by those skilled in the art of organic synthesis that one or more functional groups present in a given compound of Formula I may render the molecule incompatible with a particular synthetic sequence. In such a case an alternative route, an altered order of steps, or a strategy of protection and deprotection may be employed. In all cases the particular reaction conditions (including reagents, solvent, temperature, and time) should be chosen so that they are consistent with the nature of the functionalities present in the molecule.

As shown in Scheme 1, a suitably substituted α-amino ester 2 is treated with base and a sulfonylation or acylation agent to provide the corresponding N-blocked species. Deprotection of the ester provides the desired acid 3. Compound 3 is coupled with an appropriately elaborated amino acid ester 4 under suitable conditions to provide 5 which, upon hydrolysis, yields the target structures 6.

Scheme 1

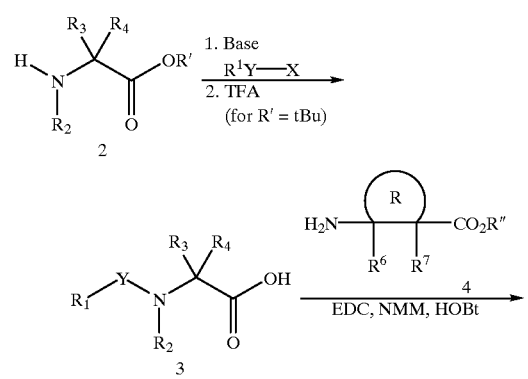

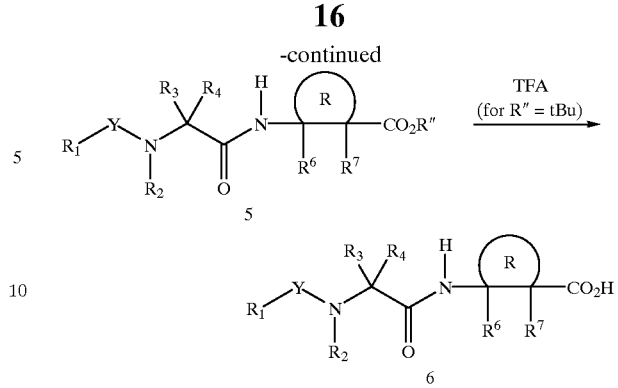

Scheme 2 addresses the syntheses of bicyclic amino acids 4aa to 4af. Appropriately substituted acrylic acid esters can be derivatized to the (E)-3-nitroacrylates 7 (J. E. McMurray et al., *Org. Syn.*, Col. V. VI, 499). When $Z^1$=H, 3-nitro cinnamic acid derivatives 8 can be obtained via reaction with an aryldiazonium salt with catalytic Pd(0) (M. Beller, et. al., *Synlett*, 1995, 441). Reaction of compounds 7 or 8 with cyclopentadiene (or another suitable diene) would produce the Diels-Alder adducts 9a and 9b. Simultaneous reduction of the C=C bond and the nitro moiety would provide 4aa or 4ab, ready for further elaboration to the target compounds 6. Alternatively, selective reduction of the nitro functionality to the amino group yields 4ac or 4ad which can be coupled with 3 to give 5. The C=C double bond in this intermediate can be further derivatized to give $(R^b)_{1-2}$ and then taken to the corresponding acids 6.

In another variation, compounds 9a or 9b can be derivatized at the double bond for example, by a hydroborationlalkylation (acylation) sequence as shown, or by a Pd(0)- or Pd(II)-mediated arylation to furnish the desired $(R^b)_{1-2}$ substituents. Subsequent reduction of the nitro moiety to the amino group provides intermediates 4ae and 4af suitable for coupling with the acid 3. Hydrolysis of the ester would provide the desired analogues 6.

Scheme 2

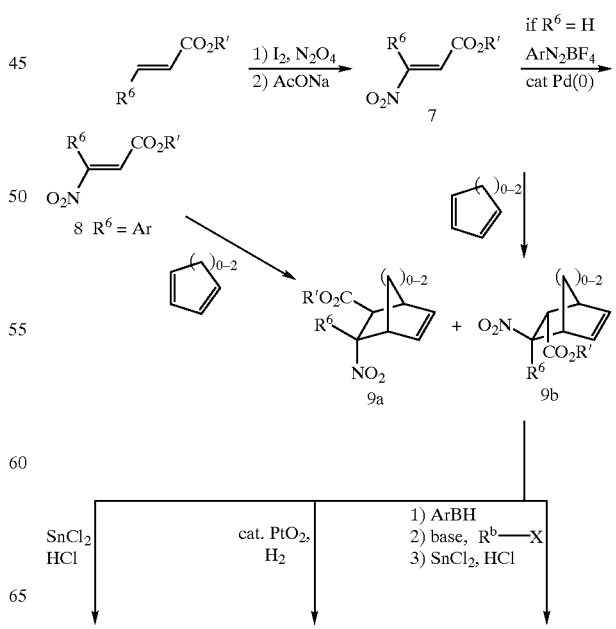

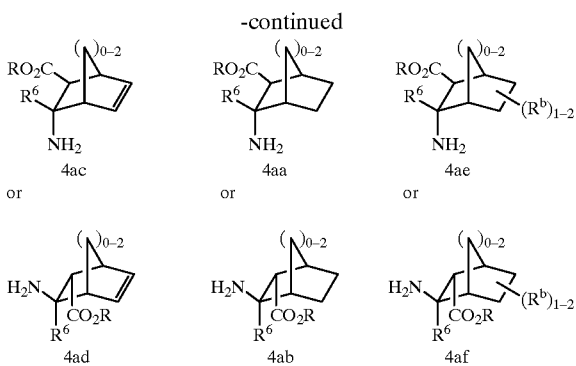

In the various synthetic methods described above, protection and deprotection of functional groups such as hydroxyl and amino groups may be required. The selection of the appropriate protecting groups, and methods for introducing and removing the protecting groups are within the knowledge of one skilled in the art, and are also described in standard reference books such as Greene and Wuts, *Protective Groups in Organic Synthesis*, 2d Ed., John Wiley & Sons, Inc., 1991.

The following examples illustrate the preparation of the compounds of Formula I and their incorporation into pharmaceutical compositions and as such are not to be construed as limiting the scope of the invention in any manner.

EXAMPLE 1

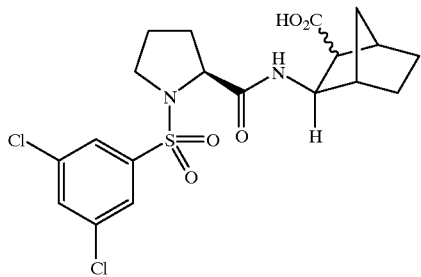

3-exo-[N-(N-3,5-Dichlorobenzenesulfonyl)-(L)-prolyl]aminobicyclo[2.2.1]heptane-2-carboxylic acid Step A: N-3,5-Dichlorobenzenesulfonyl-(L)-proline, tert-butyl ester At 0° C., to a stirred solution of 1.5 g (8.76 mmol) of (L)-proline, tert-butyl ester, 1.53 mL (8.76 mmol) of diisopropylethylamine, and 134 mg (1.75 mmol) of 4-dimethylaminopyridine dissolved in 22 mL of anhydrous dichloromethane was added dropwise a solution of 2.15 g (8.76 mmol) of 3,5-dichlorobenzenesulfonyl chloride dissolved in 8 mL of dichloromethane. The reaction mixture was allowed to warm up to room temperature overnight. Water (20 mL) was added and the phases were separated. The aqueous phase was re-extracted with dichloromethane. The combined organic extracts were washed with brine and dried over anhydrous $Na_2SO_4$. The crude product obtained after filtration and removal of volatiles was flash chromatographed through silica gel (gradient elution: 20-15/1 hexane/ethyl acetate) to give 3.23 g (97% yield) of the title compound as a white solid, homogeneous by TLC (4/1 hexane/ethyl acetate).

Mass spectrum (ESI) m/e 397.0 $(M+NH_4)^+$

400 MHz $^1$H NMR ($CDCl_3$) δ1.43 (s, 9H), 1.82–1.92 (m, 1H), 1.92–2.05 (m, 2H), 2.08–2.18 (m, 1H), 3.35–3.50 (m, 2H), 4.26 (dd, J=8.6, 3.1 Hz, 1H), 7.52 (5, J=1.8 Hz,1H), 7.72 (d, J=1.8 Hz, 2H)

Step B: N-3,5-Dichlorobenzenesulfonyl-(L)-proline

A solution of 104 mg (0.273 mmol) of N-3,5-Dichlorobenzenesulfonyl-(L)-proline, tert-butyl ester (obtained from Step A) in 2 mL of 70/30 trifluoroacetic acid/$H_2O$ was stirred between 0° C. and room temperature for 3 h. Excess trifluoroacetic acid was removed via a stream of nitrogen and the residue retreated with 2 mL of 70/30 trifluoroacetic acid/$H_2O$ and stirring was continued at room temperature for 2 h when TLC (4/1 hexane/ethyl acetate) indicated disappearance of all starting material. Excess trifluoroacetic acid was again removed via a stream of nitrogen and then coevaporated with toluene. The compound thus obtained (quantitative) was pumped in vacuo overnight and used in subsequent reactions without further purification.

Mass spectrum (ESI) m/e 278.0 $(M-CO_2)^+$

400 MHz $^1$H NMR ($CDCl_3$) δ1.85–1.95 (m, 1H), 1.95–2.12 (m, 1H), 2.12–2.23 (m, 2H), 3.31–3.37 (m, 1H), 3.47–3.53 (m, 1H), 4.38 (dd, J=8.1, 4.4 Hz, 1H), 7.56 (5, J=1.8 Hz, 1H), 7.73 (d, J=1.8 Hz, 2H), 8.97 (br s, 1H)

Step C: Ethyl 3-exo-[N-(N-3,5-Dichlorobenzenesulfonyl)-(L)-prolyl]amino-bicyclo[2.2.1]heptane-2-exo-carboxylate At room temperature, to a solution of 75 mg (0.232 mmol) of N-3,5-dichlorobenzenesulfonyl-(L)-proline (obtained from Step B) in 0.300 mL of dichloromethane was added 34.5 mg (0.255 mmol) of 1-hydroxybenzotriazole hydrate (HOBt), 64 μL (59 mg, 0.581 mmol) of N-methylmorpholine (NMM), and 61.2 mg (0.278 mmol) of ethyl 3-exo-aminobicyclo[2.2.1]heptane-2-exo-carboxylate hydrochloride. Additional dichloromethane (0.100 mL) was added to ensure complete dissolution. Subsequently, 53.5 mg (0.276 mmol) of EDC [1-(3-dimethylaminopropyl)3-ethylcarbodiimide hydrochloride] was added and the reaction mixture was allowed to stir overnight at room temperature. Water was added to quench the reaction and the organic material was extracted 3 times with ethyl acetate. The organic layers were combined and washed with water twice, brine, and dried ($MgSO_4$). The crude product obtained after filtration and removal of volatiles was chromatographed on silica gel via a Chromatotron (1000μ plate, gradient elution using 10-8-6/1 hexane/ethyl acetate) to afford 117 mg of the title compound as a sticky foam (homogeneous by TLC in 4/1 hexane/ethyl acetate; 94% yield). The doubling of the signals in the $^1$H NMR (see below) spectrum clearly indicates that this sample is a mixture of 2 diastereomers, unseparable by column chromatography.

Mass spectrum (ESI) m/e 489.2 $(M+1)^+$

400 MHz $^1$H NMR ($CDCl_3$) δ1.21–1.30 (m, 10H), 1.48–1.50 (m, 4H), 1.70–1.73 (m, 4H), 1.91 (d, J=10.5 Hz, 2H), 2.13–2.14 (m, 3H), 2.20–2.25 (m, 1H), 2.44 (s, 2H), 2.68–2.70 (m, 2H), 3.12–3.18 (m, 2H); 3.53–3.63 (m, 2H); 4.00–4.20 (m, 1H), 7.48–7.52 (m, 1H); 7.57–7.59 (m, 1H); 7.69–7.81 (m, 4H)

Step D: 3-exo-[N-(N-3,5-Dichlorobenzenesulfonyl)-(L)-prolyl]aminobicyclo-[2.2.1]heptane-2-carboxylic acid At 27° C., to a stirred solution of 30 mg (0.0613 mmol) of ethyl 3-exo-[N-(N-3,5-Dichlorobenzenesulfonyl)-(L)-prolyl]-amino-bicyclo[2.2.1]heptane-2-exo-carboxylate (obtained from Step C) in 0.600 mL of methanol was added dropwise via hypodermic 0.120 mL of 5N NaOH (0.3065 mmol). The mixture was stirred vigorously for 7 h at 27° C. when TLC (10% methanol/dichloromethane) showed consumption of all starting material. Ethyl acetate was added and the reaction mixture was acidified with 5% citric acid (aq) until pH4 was reached. After the phases were separated, the aqueous phase was extracted with ethyl acetate three times. The organic layers were combined and washed with water, brine, and dried (MgSO$_4$). The crude product obtained after filtration and removal of volatiles was purified via silica gel prep plates (eluting with 10% methanol/ dichloromethane) to afford 16 mg of product I and 2.7 mg of product II (66% total yield). Analytical HPLC (Zorbax C8RP 20 cm column, 65:35 acetonitrile/H$_2$O, λ=215 nM, flow rate=1 mL/min) of these samples revealed that Compound I consisted of two components: Ia (retention time= 20.86 min) and Ib (retention time=24.06 min). Likewise, Compound II also consisted of two components: IIa (retention time=20.54 min) and IIb (retention time=23.66 min). These were separated via HPLC on a semiprep Zorbax C8RP column and their proton NMR spectra given below.

Mass spectrum (ESI) m/e 478.3 (M+NH$_4$)$^+$

Compound Ia: 400 MHz $^1$H NMR (CD3OD) δ1.23–1.32 (m, 4H), 1.50–1.74 (m, 4H), 1.88–2.02 (m, 4H), 2.18 (d, J=3.9 Hz, 2H), 2.44 (d, J=3.0 Hz, 1H), 2.68 (d, J=7.0 Hz, 1H), 3.48–3.52 (m, 1H), 4.07–4.11 (m, 1H), 4.23 (dd, J=7.3, 4.5 Hz, 1H), 7.77 (t, J=1.8 Hz, 1H), 7.82 (d, J=1.8 Hz, 2H), 8.27 (d, J=8.4 Hz, 1H)

Compound Ib: 500 MHz $^1$H NMR (CD3OD) δ1.26 (m, 5H), 1.51–1.69 (m, 4H), 1.82–2.16 (m, 5H), 2.42 (br s, 1H), 2.67 (br s, 1H), 3.58–3.64 (m, 1H), 4.07–4.21 (m, 3H), 7.75–7.82 (m, 3H)

Compound IIa: 500 MHz $^1$H NMR (CD3OD) δ1.28 (m, 4H), 1.53–1.78 (m, 2H), 1.81–1.93 (m, 2H), 2.12–2.14 (m, 1H), 2.16–2.18 (m, 1H), 2.45 (br s, 1H), 2.68–2.72 (m, 1H), 3.50–3.60 (m, 2H), 4.08–4.12 (m, 1H), 4.22–4.25 (m, 1H), 7.77–7.85 (m, 3H), 8.28 (br s, 1H)

Compound IIb: 500 MHz $^1$H NMR (CD3OD) δ1.28–1.38 (m, 7H), 1.55–1.61 (m, 2H), 1.71–1.94 (m, 4H), 2.12 (br s, 1H), 2.44 (br s, 1H), 3.58–3.64 (m, 1H), 4.06–4.11 (m, 2H), 7.82–7.84 (m, 3H), 8.07 (br s, 1H)

EXAMPLE 2

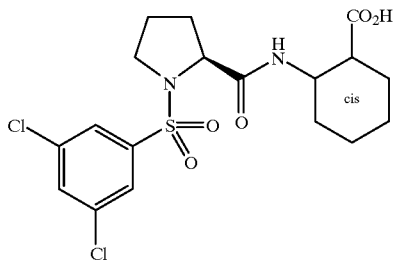

Cis-2-[N-(N-3,5-Dichlorobenzenesulfonyl)-(L)-prolyl]amino-1-cyclohexanecarboxylic acid Step A: Ethyl cis-2-[N-(N-3,5-Dichlorobenzenesulfonyl)-(L)-prolyl]amino-1-cyclohexanecarboxylate The title compound was obtained in 93% yield according to the procedure of Example 1, Step C except that ethyl cis-2-amino-1-cyclohexanecarboxylate hydrochloride was used instead of ethyl 3-exo-aminobicyclo[2.2.1]heptane-2-exo-carboxylate hydrochloride. The 2 diastereomers were obtained as an inseparable mixture.

Mass spectrum (ESI) m/e 477.3 (M+1)$^+$

300 MHz $^1$H NMR (CDCl$_3$) δ1.28 (q, J=7.1 Hz, 3H), 1.15–1.42 (m, 2H), 1.42–1.60 (m, 4H), 1.60–2.00 (m, 5H), 2.08–2.12 (m, 1H), 2.68–2.75 (m, 1H), 3.13–3.25 (m, 1H), 3.58–3.65 (m, 1H), 4.03–4.13 (m, 2H), 4.10–4.25 (m, 2H), 7.42, 7.65 (2 br d, J=7.2 Hz, 1H); 7.60 (m, 1H); 7.72, 7.73 (2 d, J=1.8 Hz, 2H)

Step B: Cis-2-[N-(N-3,5-Dichlorobenzenesulfonyl)prolyl] amino-1-cyclohexanecarboxylic acid At room temperature, to a stirred solution of 60 mg (0.126 mmol) of ethyl cis-2-[N-(N-3,5-Dichlorobenzenesulfonyl)-(L)-prolyl]amino-1-cyclo-hexanecarboxylate (obtained from Step A) in 0.600 mL of methanol was added dropwise via hypodermic 0.120 mL of 5N NaOH. The mixture was stirred vigorously for 4 h when TLC (10% methanol/DCM) showed consumption of all starting material. Ethyl acetate was added and the reaction mixture was acidified with 5% citric acid (aq) until pH5 was reached. After the phases were separated, the aqueous phase was extracted with ethyl acetate twice. The organic layers were combined and washed with water, brine, and dried (MgSO$_4$). The crude product obtained after filtration and removal of volatiles was purified via flash chromatography through silica gel (gradient elution using 1–12% methanol/dichloromethane) to afford 46 mg of the title compounds (81%) as a white powder, homogeneous by TLC (10% methanol/dichloromethane).

Mass spectrum (ESI) m/e 449.3 (M+1)$^+$

400 MHz $^1$H NMR (CD$_3$OD) δ1.42–1.75 (m, 7H), 1.75–2.10 (m, 5H), 2.68 (m, 1H), 3.30 (m, 1H), 3.55 (m, 1H), 4.03–4.28 (m, 2H), 7.79, 7.82 (2 d, J=1.9 Hz, 1H); 7.83, 7.85 (2 d, J=1.9 Hz, 2H)

EXAMPLE 3

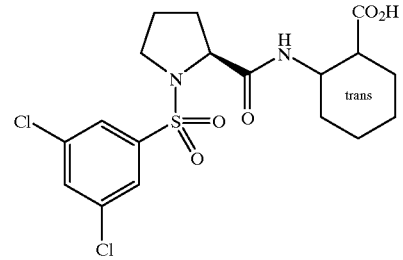

Trans-2-[N-(N-3,5-Dichlorobenzenesulfonyl)-(L)-prolyl]amino-1-cyclohexanecarboxylic acid The title compound was prepared according to the procedures of Example 2 except that ethyl trans-2-amino-1-cyclohexanecarboxylate hydrochloride was used instead of ethyl cis-2-amino-1-cyclohexanecarboxylate hydrochloride.

Mass spectrum (ESI) m/e 466.5 (M+NH$_4$)$^+$

400 MHz $^1$H NMR (CD$_3$OD) δ1.20–1.45 (m, 3H), 1.45–1.63 (m, 1H), 1.63–1.83 (m, 3H), 1.83–2.05 (m, 5H), 2.25 (m, 1H), 3.50 (m, 1H), 3.65 (m, 1H), 3.90 (m, 1H), 3.98–4.13 (m, 1H), 7.78, (m, 1H); 7.82, 7.83 (2 d, J=1.9 Hz, 2H)

EXAMPLE 4

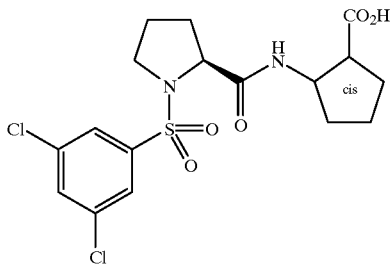

Cis-2-[N-(N-3,5-Dichlorobenzenesulfonyl)-(L)-prolyl]amino-1-cyclopentanecarboxylic acid The title compound was prepared according to the procedures of Example 2 except that ethyl cis-2-amino-1-cyclopentanecarboxylate hydrochloride (obtained from the corresponding acid by treatment with $SOCl_2$ in ethanol, G. Stajer et. al., *J. Het. Chem.* 21, 1984, 1373) was used instead of ethyl cis-2-amino-1-cyclohexanecarboxylate hydrochloride.

Mass spectrum (ESI) m/e 435.3 (M+1)$^+$

400 MHz $^1$H NMR (CD$_3$OD) δ1.60–1.83 (m, 3H), 1.83–2.12 (m, 7H), 2.96 (m, 1H), 3.30 (m, 1H), 3.55 (m, 1H), 4.12, 4.22 (2m, 1H), 4.45 (m, 1H), 7.78, (m, 1H); 7.82, (m, 2H)

EXAMPLE 5

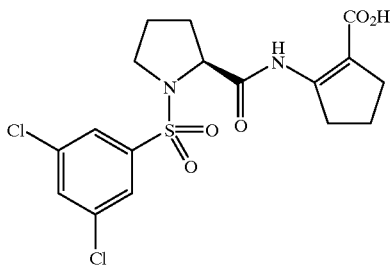

2-[N-(N-3,5-Dichlorobenzenesulfonyl)-(L)-prolyl]amino-1-cyclopentene-1-carboxylic acid The title compound was prepared according to the procedures of Example 2 except that ethyl 2-amino-1-cyclopentene-1-carboxylate hydrochloride was used instead of ethyl cis-2-amino-1-cyclohexanecarboxylate hydrochloride.

Mass spectrum (ESI) ml/e 450.4 (M+NH$_4$)$^+$

400 MHz $^1$H NMR (CD$_3$OD) δ1.80–2.15 (m, 6H), 2.50 (m, 2H), 3.06 (m, 2H), 3.42 (m, 1H), 3.65 (m, 1H), 4.23 (dd, J=8, 3 Hz, 1H), 7.80, (d, J=1.8 Hz, 1H); 7.81, (d, J=1.8 Hz, 2H)

EXAMPLE 6

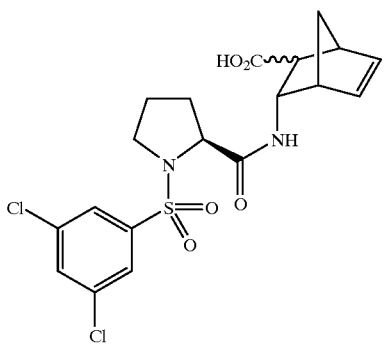

3-endo-[N-(N-3,5-Dichlorobenzenesulfonyl)-(L)-prolyl]amino-bicyclo[2.2.1]-hept-5-ene-2-carboxylic acid The title compound was prepared according to the procedures of Example 2 except that ethyl 3-endo-aminobicyclo[2.2.1]-hept-5-ene-2-endo-carboxylate hydrochloride was used instead of ethyl cis-2-amino-1-cyclohexanecarboxylate hydrochloride. Two fractions were obtained from column chromatography purification, Compound VIa (ratio of the less polar/more polar acid is 2:1), and Compound VIb (ratio of the less polar/more polar acid is 1:2:3).

Mass spectrum (ESI) m/e 459.4 (M+1)$^+$

Compound VIa: 400 MHz $^1$H NMR (CD$_3$OD) δ1.40–1.55 (m, 2H), 1.65–2.00 (m, 4H), 3.154–3.23 (m, 4H), 3.30 (m, 1H), 3.53 (m, 1H), 4.08, 4.14 (2 dd, J=8.0, 3.3 Hz, 1H), 4.51, 4.62 (2 m, 1H), 6.14, 6.22 (2 dd, J=5.7, 2.9 Hz, 1H), 6.34, 6.38 (2 dd, J=5.7, 2.4 Hz, 1H), 7.77, 7.80, (2 t, J=1.9 Hz, 1H); 7.80, 7.82 (2 d, J=1.9 Hz, 2H)

Compound VIb: 400 MHz $^1$H NMR (CD$_3$OD) δ1.40–1.55 (m, 2H), 1.65–2.00 (m, 4H), 3.154–3.23 (m, 4H), 3.30 (m, 1H), 3.53 (m, 1H), 4.08, 4.14 (2 dd, J=8.0, 3.3 Hz, 1H), 4.51, 4.62 (2 m, 1H), 6.14, 6.22 (2 dd, J=5.7, 2.9 Hz, 1H), 6.34, 6.38 (2 dd, J=5.7, 2.4 Hz, 1H), 7.77, 7.80, (2 t, J=1.9 Hz, 1H); 7.80, 7.82 (2 d, J=1.9 Hz, 2H)

EXAMPLE 7

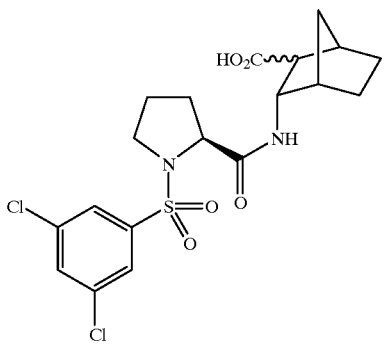

3-endo-[N-(N-3,5-Dichlorobenzenesulfonyl)-(L)-prolyl]amino-bicyclo[2.2.1]-heptane-2-carboxylic acid Step A: Ethyl 3-endo-[N-(N-3,5-Dichlorobenzenesulfonyl)-(L)-prolyl]amino-bicyclo[2.2.1]heptane-2-endo-carboxylate At room temperature, to a solution of 255 mg (0.791 mmol) of N-3,5-dichlorobenzenesulfonyl-(L)-proline (obtained from Example 1, Step B) in 3.0 mL of DCM was added 118 mg (0.869 mmol) of 1-hydroxybenzotriazole hydrate, 212 μL (201 mg, 1.98 mmol) of N-methylmorpholine, and 209 mg (0.948 mmol) of ethyl 3-endo-amino-bicyclo[2.2.1]heptane-2-endo-carboxylate hydrochloride. Subsequently, 197 mg (1.03 mmol) of [1-(3-dimethylaminopropyl)3-ethylcarbodiimide hydrochloride] was added and the reaction mixture was allowed to stir overnight at 27° C. Water was added to quench the reaction and the organic material was extracted 3 times with ethyl acetate. The organic layers were combined and washed with water twice, brine, and dried (MgSO$_4$). The crude product obtained after filtration and removal of volatiles was flash chromatographed over silica gel (60 mL, gradient elution using hexane/ethyl acetate) to afford 155 mg (40%) of a clean fraction of the less polar diastereomer (diastereomer IIIa), 96 mg (25%) of a clean fraction of the more polar diastereomer (diastereomer IIIb), and 139 mg (35%) of a mixture of the two diastereomers.

Mass spectrum (ESI) m/e 489.4 (M+1)$^+$

Diastereomer IIIa: 400 MHz $^1$H NMR (CDCl$_3$) δ1.25 (t, J=6.8 Hz, 3H), 1.37–1.48 (m, 3H), 1.49–1.52 (m, 3H), 1.76–1.81 (m, 2H), 1.82–1.91 (m, 1H), 2.02–2.10 (m, 1H), 2.54 (br s, 2H), 2.93 (dd, J=10.6, 4.3 Hz, 1H), 3.20–3.22 (m, 1H); 3.66–3.71 (m, 1H); 4.07–4.10 (m, 1H), 4.13–4.23 (m, 3H), 7.56 (t, J=1.8 Hz, 1H); 7.71 (d, J=1.8 Hz, 2H); 8.83 (d, J=6.8 Hz, 1)

Diastereomer IIIb: 400 MHz $^1$H NMR (CDCl$_3$) δ1.23 (t, J=7.0 Hz, 3H), 1.37–1.57 (m, 5H), 1.66–1.81 (m, 4H), 2.09–2.13 (m, 1H), 2.54 (br s, 2H), 2.89 (dd, J=11.0, 4.4 Hz, 1H), 3.18–3.25 (m, 1H); 3.61–3.66 (m, 1H); 4.07–4.18 (m, 3H), 4.19–4.24 (m, 1H), 7.57 (t, J=1.8 Hz, 1H); 7.75 (d, J=1.8 Hz, 2H); 8.71 (d, J=7.6 Hz, 1H)

Step B: 3-endo-[N-(N-3,5-Dichlorobenzenesulfonyl)-(L)-prolyl]-aminobicyclo[2.2.1]heptane-2-carboxylic acid Each of the diastereomers of ethyl 3-endo-[N-(N-3,5-dichlorobenzenesulfonyl)prolyl]aminobicyclo[2.2.1] heptane-2-endo-carboxylate (Diastereomer IIIa and Diastereomer IIIb obtained from Step A) was saponified to the corresponding acid according to the procedure of Example 1 Step D. Diastereomer IIIa afforded a 47% of a white foam, homogeneous by TLC (10% methanol/dichloromethane). However, analytical HPLC (Zorbax C8RP 20 cm column, 65:35 acetonitrile/H$_2$O, λ=215 nM, flow rate=1 mL/min)) indicated that there were two components in the ratio of 1:2: Compounds IVa (retention time=21.36 min) and IVb (retention time=26.00 min). These were separated by semi-prep HPLC on a Zorbax C8RP column. The saponification of Diastereomer IIIb gave a 28% of a light brown foam, homogeneous by TLC (10% methanol/dichloromethane). However, HPLC (same conditions as above) revealed two components: Compounds IVc and IVd. These were also passed through the semiprep Zorbax RPC8 column, although the separation was not complete in this case. The proton NMR spectra of these compounds (assumed to be two pairs of epimers arising from epimerization under the saponification conditions) are recorded below.

Mass spectrum (ESI) m/e 478.3 (M+NH$_4$)$^+$

Compound VIIa: 400 MHz $^1$H NMR (CD3OD) δ1.28–1.49 (m, 4H), 1.50–1.58 (m, 4H), 1.79–1.81 (m, 1H), 1.89–2.00 (m, 3H), 2.54–2.57 (m, 2H), 2.96 (dd, J=10.4, 4.4 Hz, 1H), 3.59–3.64 (m, 1H), 4.01–4.06 (m, 1H), 4.16 (dd, J=7.7, 3.4 Hz, 1H), 7.80–7.82 (m, 3H), 9.28–9.29 (m, 1H)

Compound VIIb: 400 MHz $^1$H NMR (CD3OD) δ1.32–1.51 (m, 4H), 1.62–1.74 (m, 4H), 1.92–2.02 (m, 3H), 2.12 (dd, J=5.2, 1.8 Hz, 1H), 2.48 (d, J=3.7 Hz, 1H), 2.52 (br s, 1H), 3.33–3.37 (m, 1H), 3.49–3.53 (m, 1H), 4.17–4.23 (m, 2H), 7.78 (t, J=1.8 Hz, 1H), 7.82 (d, J=2.0 Hz, 2H), 8.32 (d, J=6.6 Hz, 1H)

Compound VIIc (mainly the more polar component): 400 MHz $^1$H NMR (CD3OD) δ1.21–1.78 (m, 4H), 1.79–2.19 (m, 4H), 2.18–2.23 (m, 1H), 2.42–2.51 (m, 3H), 2.51–2.57 (m, 1H), 2.91–2.94 (m, 1H), 3.51–3.68 (m, 2H), 4.07–4.25 (m, 2H), 7.78–7.86 (m, 3H), 9.61–9.68 (m, 1H)

Compound VIId (mainly the less polar component): 400 MHz $^1$H NMR (CD3OD) δ1.26–1.47 (m, 4H), 1.70–2.14 (m, 4H), 2.20–2.21 (m, 1H), 2.46–2.49 (m, 3H), 2.58–2.59 (m, 1H), 2.90–2.99 (M, 1H), 3.53–3.57 (m, 1H), 4.12–4.24 (m, 3H), 7.78–7.86 (m, 3H), 9.30–9.35 (m, 1H)

EXAMPLE 8

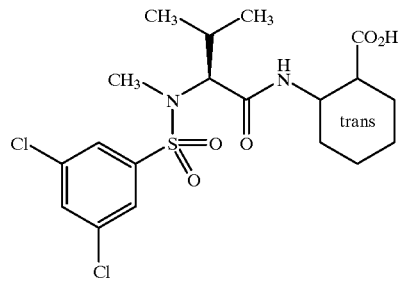

Trans-2-[N-(N-3,5-Dichlorobenzenesulfonyl-N-methyl)-(L)-valyl]amino-1-cyclohexanecarboxylic acid The title compound was prepared according to the procedures of Example 3 except that (N-3,5-dichlorobenzenesulfonyl-N-methyl)valine (obtained from N-methylvaline t-butyl ester according to the procedure of Example 1 Steps A–B) was used instead of N-3,5-dichlorobenzenesulfonyl-(L)-proline. Two products with identical mass spectra were isolated after base hydrolysis of the ester, Compound Va (less polar) and Compound Vb (more polar).

Mass spectrum (ESI) m/e 482.3 (M+NH$_4$)$^+$

Compound VIIIa: 400 MHz $^1$H NMR (CDCl$_3$) δ0.56 (d, J=6.4 Hz, 3H), 0.87 (d, J=6.4 Hz, 3H), 0.77–1.00 (m, 2H), 1.15–1.45 (m, 2H), 1.45–1.85 (m, 2H), 1.85–2.1 (m, 2H), 2.15 (m, 1H), 2.40 (m, 1H), 2.84 (s, 3H), 3.71 (d, J=10 Hz, 1H), 3.90 (m, 1H), 6.15 (s, 1H), 7.52, (s, 1H); 7.65 (br s, 2H)

Compound VIIIb: 400 MHz $^1$H NMR (CDCl$_3$) δ0.65 (d, J=6.5 Hz, 3H), 0.84 (d, J=6.5 Hz, 3H), 1.15–1.85 (m, 6H), 1.90–2.05 (m, 2H), 2.15 (m, 1H), 2.35 (m, 1H), 2.88 (s, 3H), 3.65 (d, J=11 Hz, 1H), 3.95 (m, 1H), 5.87 (d, J=8 Hz, 1H), 7.53, (m, 1H); 7.64 (d, J=1.8 Hz, 2H)

EXAMPLE 9

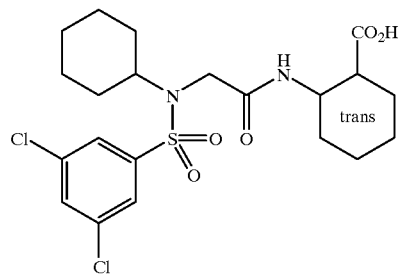

Trans-2-[N-(N-Cyclohexyl-N-3,5-Dichlorobenzenesulfonyl)glycyl]amino-1-cyclohexanecarboxylic acid The title compound was prepared according to the procedures of Example 3 except that (N-cyclohexyl-N-3,5- dichlorobenzenesulfonyl)glycine (obtained from N-cyclohexylglycine, tert-butyl ester according to the procedure of Example 1 Steps A–B) was used instead of N-3,5-dichlorobenzene-sulfonyl-(L)-proline.

Mass spectrum (ESI) m/e 508.3 (M+NH$_4$)$^+$

400 MHz $^1$H NMR: (CD$_3$OD) δ0.95–1.15 (m, 2H), 1.15–1.45 (m, 6H), 1.45–1.65 (m, 4H), 1.65–1.85 (m, 4H), 1.85–2.08 (m, 2H), 2.30 (m, 1H), 3.60 (m, 1H), 3.90 (m, 2H), 7.73, (s, 1H); 7.91 (s, 2H)

EXAMPLE 10

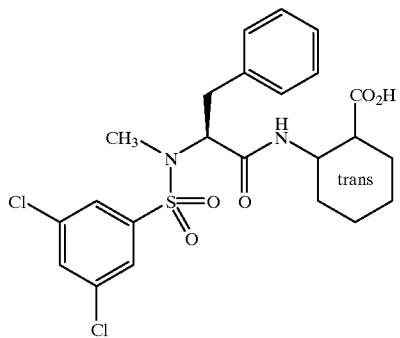

Trans-2-[N-(N-3,5-Dichlorobenzenesulfonyl-N-methyl)-(L)-phenylalanyl]amino-1-cyclohexanecarboxylic acid The title compound was prepared according to the procedures of Example 3 except that (N-3,5-dichlorobenzenesulfonyl-(L)-N-methyl)phenylalanine (obtained from (L)-N-methylphenylalanine, tert-butyl ester according to the procedure of Example 1 Steps A–B) was used instead of N-3,5-dichlorobenzene-sulfonyl-(L)-proline.

Mass spectrum (ESI) m/e 530.4 (M+NH$_4$)$^+$

400 MHz $^1$H NMR: (CDCl$_3$) δ0.70–1.65 (m, 6H), 1.72 (m, 1H), 1.95 (m, 1H), 2.45 (m, 1H), 2.70 (m, 1H), 2.90, 2.92 (2 s, 3H), 3.15, 3.23 (2 dd J=14, 7 Hz, 1H), 4.00 (m, 1H), 4.53 (m, 1H), 6.25, 6.38 (2 br s, 1H), 6.90–7.03 (m, 2H), 7.05–7.20 (m, 3H), 7.27 (m, 2H), 7.38 (m, 1H)

EXAMPLE 11

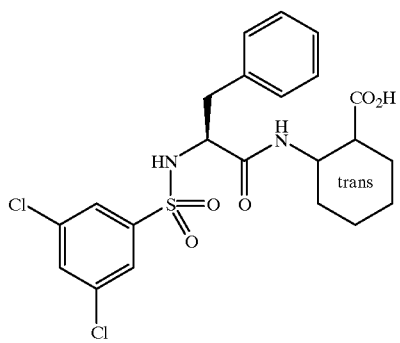

Trans-2-[N-(N-3,5-Dichlorobenzenesulfonyl)-(L)-phenylalanyl]amino-1-cyclohexanecarboxylic acid The title compound was prepared according to the procedures of Example 3 except that (N-3,5-dichlorobenzenesulfonyl)-phenylalanine (obtained from (L)-phenylalanine t-butyl ester according to the procedure of Example 1 Steps A–B) was used instead of N-3,5-dichlorobenzene-sulfonyl-(L)-proline.

Mass spectrum (ESI) m/e 516.3 (M+NH$_4$)$^+$

400 MHz $^1$H NMR: (CD$_3$OD) δ0.70–1.00 (m, 1H), 1.10–1.45 (m, 4H), 1.45–1.65 (m, 1H), 1.65–1.85 (m, 2H), 2.18 (m 1H), 2.57, 2.68 (2 dd J=13.8, 10.6 Hz, 1H), 2.91, 3.02 (2 dd J=14.0, 3.3 Hz, 1H), 3.91–4.05 (m, 2H), 6.98–7.03 (m, 2H), 7.03–7.18 (m, 3H), 7.43, 7.44 (2 d, J=2.0 Hz, 2H), 7.53, 7.54 (2 t, J=2.0 Hz, 1H)

EXAMPLE 12

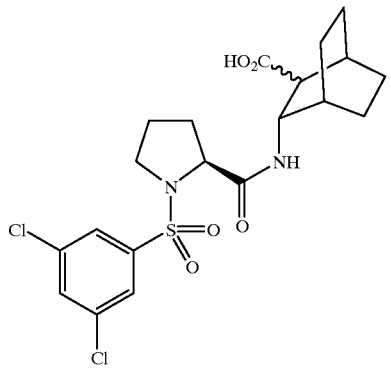

3-endo-[N-(N-3,5-Dichlorobenzenesulfonyl)-(L)-prolyl]amino-bicyclo[2.2.2]-octane-2-carboxylic acid Step A: Methyl 3-nitrobicyclo[2.2.2]oct-5-en e-2-carboxvylate A solution of methyl (E)-3-nitroacrylate (1.17 g, 9 mmol, prepared according to McMurry, J. E., et. al, Org. Syn. Col. Vol. VI, p.799) and 1,3-cyclohexadiene (9 mL) was placed in a sealed tube and heated to 130° C. for 60 min. The volatiles were removed under reduced pressure and the crude product was flash chromatographed over silica gel to provide four fractions containing 6.1:1 (mixture I) and 4.2:1 (mixture II) of methyl 3-endo-nitrobicyclo[2.2.2]oct-5-ene-2-exo-carboxylate vs. methyl 3-exo-nitrobicyclo[2.2.2]oct-5-ene-2-endo-carboxylate in a total yield of 1.65 g (95%).

Mass spectrum (EI) m/e 211 (M)$^+$

400 MHz $^1$H NMR for methyl 3-endo-nitrobicyclo[2.2.2]oct-5-ene-2-exo-carboxylate: (CDCl$_3$) δ1.05–1.25 (m, 1H), 1.35–1.45 (m, 2H), 1.58–1.68 (m, 1H), 3.06 (m, 1H), 3.20 (m, 1H), 3.40 (m, 1H), 3.74 (s, 3H), 5.05 (t, J=3.5 Hz, 1H), 6.13 (t, J=6.7 Hz, 1H), 6.42 (t, J=7.0 Hz, 1H)

400 MHz $^1$H NMR for methyl 3-exo-rntrobicyclo[2.2.2]oct-5-ene-2-endo-carboxylate: (CDCl$_3$) δ1.20–1.30 (m, 2H), 1.46–1.56 (m, 1H), 1.68–1.78 (m, 1H), 3.12 (m, 1H), 3.32 (m, 1H), 3.48 (m, 1H), 3.66 (s, 3H), 4.80 (m, 1H), 6.25 (m, 2H)

Step B: Methyl 3-endo-nitrobicyclo[2.2.2]octane-2-exo-carboxylate

Methyl 3-nitrobicyclo[2.2.2]oct-5-ene-2-carboxylate (550 mg, 1.18 mmol, mixture I obtained from Step A) was dissolved in ethyl acetate (4.4 mL), degassed and filled with hydrogen and platinum oxide (20 mg) was added. The resulting mixture was hydrogenated under a balloon of hydrogen at room temperature for 4 h. TLC (10:1 hexane/ethyl acetate) showed that all of the starting material had disappeared. The catalyst was removed over a pad of celite to give an oil in quantitative yield. This material had MS and $^1$H NMR consistent with the desired compound and was used in the next experiment without further purification.

Mass spectrum (EI) m/e 213 (M)$^+$
400 MHz $^1$H NMR: (CDCl$_3$) δ1.30–1.50 (m, 4H), 1.50–1.75 (m, 4H), 2.21 (m, 1H), 2.47 (m, 1H), 3.06 (m, 1H), 3.20 (m, 1H), 3.49 (dt, J=5.9, 2.0 Hz, 1H), 3.72 (s, 3H), 5.05 (dd, J=5.8, 2.3 Hz, 1H)

Step C: Methyl 3-endo-aminobicyclo[2.2.2]octane-2-exo-carboxylate

A solution of methyl 3-endo-nitrobicyclo[2.2.2]octane-2-exo-carboxylate (200 mg, 0.94 mmol, obtained from Step B) in methanol (2.0 mL) was degassed and filled with nitrogen. After the addition of 10 Pd/C (20 mg) the degas/nitrogen fill process was repeated twice. Subsequently, ammonium formate (630 mg, 10 mmol) was added and the heterogeneous mixture was stirred at room temperature for 7 h. Since TLC (10% methanol in dichloromethane) suggested possibly some starting material was left, addition amounts of catalyst (10 mg) and ammonium formate (300 mg) was added and the mixture stirred for another hour. The reaction was filtered over a pad of celite washed with ether and ethyl acetate. The filtrate was washed with water and brine and dried over anhydrous sodium sulfate. After filtration and removal of volatiles, the crude product was flash chromatographed over silica gel (gradient elution using 0.25–5% methanol in methylene chloride) to give 85 mg (42% yield) of the desired amino compound and 65 mg (32%) of the partially reduced hydroxyamino compound. For ensure compound stability, the desired product was treated with HCl(gas)/ethyl acetate to form the HCl salt. Mass spectrum (EI) m/e 183 (M)$^+$ 400 MHz $^1$H NMR: (CDCl$_3$) δ1.30–1.65 (m, 8H), 1.70–1.85 (m, 1H), 1.95–20 (m, 1H), 2.10–2.17 (m, 1H), 2.21 (m, 1H), 3.30–3.35 (m, 1H), 3.70 (s, 3H)

Step D: Methyl 3-endo-[N-(N-3,5-dichlorobenzenesulfonyl)-(L)-prolyl]aminobicyclo[2.2.2]-octane-2-carboxylate At room temperature, to a solution of 126 mg (0.39 mmol) of N-3,5-dichlorobenzenesulfonyl-(L)-proline (obtained from Example 1 Step B) in 2.0 mL of dichloromethane was added 58 mg (0.43 mmol) of 1-hydroxybenzotriazole hydrate (HOBt), 108 μL (99 mg, 0.975 mmol) of N-methylmorpholine (NMM), and 85 mg (0.39 mmol) of methyl 3-endo-aminobicyclo[2.2.2]octane-2-exo-carboxylate hydrochloride (obtained from Step C). Additional dichloromethane (0.100 mL) was added to ensure complete dissolution. Subsequently, 90 mg (0.47 mmol) of EDC [1-(3-dimethylaminopropyl)3-ethylcarbodiimide hydrochloride] was added and the reaction mixture was allowed to stir overnight at room temperature. TLC (2:1 hexane/ethyl acetate) suggested a lot of starting acid left. Therefore, one more equivalent of EDC was added along with 0.8 equivalents of NMM. After another day of stirring, water was added to quench the reaction and the organic material was extracted 3 times with ethyl acetate. The organic layers were combined and washed with water twice, brine, and dried (MgSO$_4$). The crude product obtained after filtration and removal of volatiles was flash chromatographed over silica gel to afford 134 mg (70%) of the title compound as a tacky solid (homogeneous by TLC in 2/1 hexane/ethyl acetate). The doubling of the signals in the $^1$H NMR (see below) spectrum clearly indicates that this sample is a mixture of 2 diastereomers, unseparable by column chromatography.

Mass spectrum (ESI) m/e 489.2 (M+1)$^+$
500 MHz $^1$H NMR (CDCl$_3$) δ1.38–1.48 (m, 1H), 1.48–1.90 (m, 10H), 1.97–2.06 (m, 1H), 2.26–2.43 (m, 2H), 3.14–3.22 (m, 1H), 3.57–3.66 (m, 1H), 3.72,3.74 (2s, 3H), 4.05 (dt, J=8.7, 2.8 Hz, 1H),4.30–4.42 (m, 1H) 7.64 (t, J=4.4 Hz, 1H), 7.72 (d, J=1.9 Hz, 2H)

Step E: 3-endo-[N-(N-3,5-Dichlorobenzenesulfonyl)-(L)-prolyl]aminobicyclo[2.2.2]-octane-2-exo-carboxylic acid To a solution of methyl 3-endo-[N-(N-3,5-dichlorobenzenesulfonyl)-(L)-prolyl]aminobicyclo[2.2.2]-octane-2-carboxylate (70 mg, 0.143 mmol, from Step D) in 0.30 mL of methanol was added dropwise 29 gL of 5N aqueous NaOH. The reaction mixture was allowed to stir at room temperature for 4 days when TLC showed finally the disappearance of all starting material. The volatiles were removed under reduced pressure and the residue was diluted with dichloromethane, acidified to pH4–5 using 5% citric acid. The phases were separated and the aqueous layer was extracted with dichloromethane twice more. The organic layers were combined and washed with brine and dried over anhydrous sodium sulfate. The crude product obtained after filtration and removal of volatiles was flash chromatographed to give 3 fractions: Fraction I is one of the 3-endo-[N-(N-3,5-dichlorobenzenesulfonyl)-(L)-prolyl]aminobicyclo[2.2.2]-octane-2-endo-carboxylic acid isomers, Fraction II is a 9:5 mixture (by $^1$H NMR) of the isomers of 3-endo-[N-(N-3,5-dichlorobenzenesulfonyl)-(L)-prolyl]aminobicyclo[2.2.2]-octane-2-exo-carboxylic acid, and Fraction III is the other isomer of 3-endo-[N-(N-3,5-dichlorobenzenesulfonyl)-(L)-prolyl]aminobicyclo[2.2.2]-octane-2-endo-carboxylic acid as determined by their $^1$H NMR spectra.

Mass spectrum (ESI) m/e 475.2 (M+1)$^+$ (for all fractions).

Fraction I: 400 MHz $^1$H NMR (CD$_3$OD) δ1.40–1.52 (m, 2H), 1.52–1.85– (m, 8H), 1.90–2.15 (m, 4H), 2.42 (d, J=6.4 Hz, 1H), 3.30–3.40 (m, 1H), 3.50–3.60 (m, 1H), 4.17 (dd, J=7.8, 4.5 Hz, 1H), 4.26 (dt, J=6.5, 1.2 Hz, 1H), 7.78, (t, J=1.8 Hz, 1H), 7.81 (d, J=1.7 Hz, 2H).

Fraction II: 500 MHz $^1$H NMR (CD$_3$OD) δ1.38–1.54 (m, 2H), 1.54–1.82– (m, 8H), 1.90–2.15 (m, 4H), 2.38–2.54 (m, 1H), 3.25–3.22 (m, 1H), 3.49–3.60 (m, 1H), 4.11–4.21 (m, 1H), 4.23–4.35 (m, 1H), 7.74, 7.75 (2t, J=2.0 Hz, 1H), 7.80, 7.82 (2d, J=1.8 Hz, 2H).

Fraction III: 400 MHz $^1$H NMR (CD$_3$OD) δ1.35–1.52 (m, 2H), 1.52–1.85– (m, 8H), 1.85–2.08 (m, 4H), 2.38 (d, J=6.0 Hz, 1H), 3.20–3.40 (m, 1H), 3.50–3.65 (m, 1H), 4.13 (m, 1H), 4.45 (m, 1H), 7.81, (t, J=1.9 Hz, 1H), 7.84 (d, J=1.7 Hz, 2H).

EXAMPLE 13

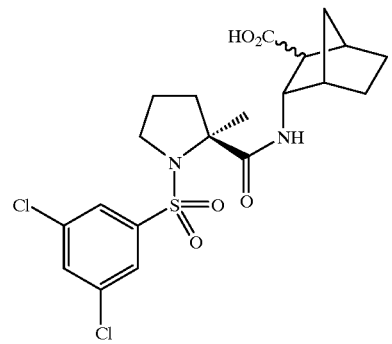

3-endo-N-(N-3,5-Dichlorobenzenesulfonyl)-(L)-2 (S)-methyl-prolyl]amino-bicyclo[2.2.1]-heptane-2-carboxylic acid Step A: Ethyl 3-endo-[N-(N-3,5-Dichlorobenzenesulfonyl)-(L)-2(S)-methyl-prolyl]amino-bicyclo[2.2.1]heptane-2-endo-carboxylate At room temperature, to a solution of 50 mg (0.148 mmol) of N-3,5-dichlorobenzenesulfonyl-(L)-2(S)-methyl-proline (prepared in an analogous manner to N-3,5-dichlorobenzenesulfonyl-(L)-proline except that a-methyl proline t-butyl ester was used instead of proline t-butyl ester) in 1.5 mL of dichloromethane was added 33 mg (0.148 mmol) of ethyl 3-endo-aminobicyclo[2.2.1]heptane-2-endo-carboxylate hydrochloride, 48 mg (0.375 mmol) of diisopropylethylamine, and 86 mg (0.165 mmol) of benzotriaol-1-yloxytripyrrolidinophosphonium hexafluorophosphate. The reaction mixture was allowed to stir overnight at room temperature. Dichloromethane was added to dilute the reaction mixture and 5% citric acid (aqueous) was added. The phases were separated and the aqueous phase was re-extracted twice using methylene chloride. The organic layers were combined and washed with saturated aqueous sodium bicarbonate five times followed by water and brine and dried over anhydrous sodium sulfate. The crude product obtained after filtration and removal of volatiles was flash chromatographed on silica gel (gradient elution using 15-5/1 hexane/ethyl acetate). The two diastereomers were not separable by this method. The mixtures obtained in this manner were separated via prep TLC (two 1500 micron plates, 4:1 hexane/ethyl acetate, eluted 4 times) to afford two fractions. The less polar diastereomer (Fraction 1) was obtained in 25 mg yield cleanly and the more polar diastereomer (Fraction 2) was obtained in 35 mg yield, also clean by TLC and NMR.

Mass spectrum (ESI) m/e 503.2 (M+1)+ for both fractions

Fraction 1: 500 MHz $^1$H NMR (CDCl$_3$) δ1.28 (t, J=−7.1 Hz, 3H), 1.42–1.50 (mn 4H), 1.53–1.58 (mn, 1H), 1.60–1.66 (mn, 1H), 1.8 (s, 3H), 1.80–1.87 (m, 1H), 1.90–1.98 (m, 1H), 2.00–2.10 (m, 1H), 2.30–2.37 (mn, 1H), 2.58 (br s, 1H), 2.70 (br s, 1H), 2.95 (dd, J=11, 4.3 Hz, 1H), 3.51 (dd, J=12, 7.1 Hz, 1H), 3.65–3.72 (mn, 1H), 4.10–4.21 (mn, 3H), 7.52 (t, J=1.7 Hz, 1H), 7.74 (d, J=1.8 Hz, 2H), 8.62(d, J=6.1 Hz, 1H)

Fraction 2: 500 MHz $^1$H NMR (CDCl$_3$) δ1.27 (t, J=7.1 Hz, 3H), 1.39–1.50 (mn 3H), 1.50–1.58 (mn, 2H), 1.67 (s, 3H), 1.76–1.98 (mn, 3H), 2.30–2.38 (m, 1H), 2.54–2.62 (mn, 2H), 2.96 (dd, J=10.7, 4.5 Hz, 1H), 3.40 (dd, J=15.6, 8.2 Hz, 1H), 3.75 (td, J=8.0, 4.2 Hz, 1H), 4.10–4.30 (m, 3H), 7.55 (t, J=1.9 Hz, 1H), 7.78 (d, J=1.7 Hz, 2H), 8.60(d, J=7.6 Hz, 1H)

Step B: 3-Endo-N-(N-3,5-Dichlorobenzenesulfonyl)-(L)-2(S)-methyl-prolyl]amino-bicyclo[2.2.1]-heptane-2-carboxylic acid Each of the isomers obtained from Step A was subjected to base hydrolysis as described in Example 1 Step D except that the reactions were run at 30° C. overnight. The two crude mixtures were each separated via a 1000 micron prep TLC plate to provide 4 diastereomers. Diastereomer 1a (less polar, 43% yield) and Diastereomer 1b (more polar, 45% yield) resulted from Fraction 1 of Step A. Diastereomer 2a (less polar, 30% yield) and Diastereomer 2b (more polar, 40% yield) were obtained from Fraction 2 of Step A. The stereochemistry at the carboxylic acid-bearing carbon was assigned based on comparisons of NMR data for similar structures obtained from the foregoing examples.

Mass spectrum (ESI) m/e 475.3 (M+1)+ for all four diastereomers.

Diastereomer 1a (3-endo-N-(N-3,5-Dichlorobenzenesulfonyl)-(L)-2(S)-methyl-prolyl]amino-bicyclo[2.2.1]-heptane-2-exo-carboxylic acid:

500 MHz $^1$H NMR (CD$_3$OD) δ1.26–1.38 (m, 2H), 1.40–1.56 (m, 2H), 1.62 (s, 3H), 1.63–1.76 (m, 2H), 1.84–1.98 (m, 3H), 2.22–2.30 (m, 2H), 2.50 (br d, 1H), 2.57 (br s, 1H), 3.45 (dd, J=16, 7.0 Hz, 1H), 3.58–3.65 (m, 1H), 4.18–4.24 (m, 1H), 7.50 (d, J=5.7 Hz, 1H), 7.75 (t, J=1.9 Hz, 1H), 7.79 (d, J=1.9 Hz, 2H)

Diastereomer 1b (3-endo-N-(N-3,5-Dichlorobenzenesulfonyl)-(L)-2(S)-methyl-prolyl]amino-bicyclo[2.2.1]-heptane-2-endo-carboxylic acid:

500 MHz $^1$H NMR (CD$_3$OD) δ1.30–1.60 (m, 6H), 1.64 (s, 3H), 1.88–2.06 (m, 3H), 2.17–2.24 (m, 1H), 2.59 (br s, 1H), 2.69 (br s, 1H), 2.92 (m, 1H), 3.54–3.62 (m, 1H), 3.92–3.98 (dd, J=10.6, 5.3 Hz, 1H), 7.71 (t, J=1.8 Hz, 1H), 7.74 (d, J=1.9 Hz, 2H), 9.56 (s, 1H)

Diastereomer 2a (3-endo-N-(N-3,5-Dichlorobenzenesulfonyl)-(L)-2(S)-methyl-prolyl]amino-bicyclo[2.2.1]-heptane-2-exo-carboxylic acid:

500 MHz $^1$H NMR (CD$_3$OD) δ1.39–1.50 (m, 2H), 1.59 (s, 3H), 1.60–1.76 (m, 3H), 1.82–1.96 (m, 3H), 2.22–2.31 (m, 2H), 2.50 (br s, 2H), 3.41 (dd, J=16.2, 7.3 Hz, 1H), 3.65–3.71 (m, 1H), 4.24–4.29 (m, 1H), 7.76 (t, J=1.9 Hz, 1H), 7.81 (d, J=2 Hz, 2H)

Diastereomer 1b (3endo-N-(N-3,5-Dichlorobenzenesulfonyl)-(L)-2(S)-methyl-prolyl]amino-bicyclo[2.2.1]-heptane-2-endo-carboxylic acid:

500 MHz $^1$H NMR (CD$_3$OD) δ1.30–1.50 (m, 3H), 1.60 (s, 3H), 1.52–1.68 (m, 2H), 1.75–2.08 (m, 4H), 2.14–2.24 (m, 1H), 2.50 (br s, 1H), 2.59 (br s, 1H), 2.95 (m, 1H), 3.36–3.48 (m, 1H), 3.54–3.60 (m, 1H), 3.68–3.76 (m, 1H), 4.04–4.14 (m, 1H), 7.75 (m, 1H), 7.81 (d, J=1.8 Hz, 2H), 9.49 (br s, 1H)

EXAMPLE 14

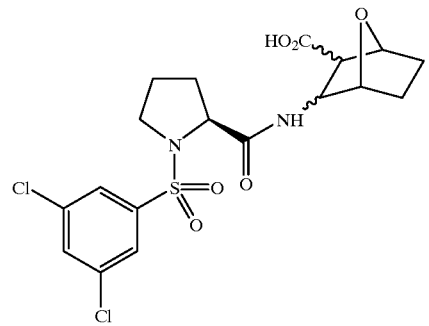

3exo-[N-(N-3,5-Dichlorobenzenesulfonyl)-(L)-proly]amino-7-oxobicyclo[2.2.1]-heptane-2-carboxylic acid and 3-endo-[N-(N-3,5-dichlorobenzenesulfonyl)-(L)-prolyl]amino-7-oxobicyclo[2.2.1]-heptane-2-carboxylic acid Step A: endo/exo-3-Amino-7-oxobicyclo[2.2.1]heptane-2-carboxylate, methyl ester To an endo/exo mixture (3:2 ratio) of methyl 2-nitro-7-oxobicyclo[2.2.1]hept-5-ene-1-carboxylate (0.64 g, prepared following the procedure of Grieco, P A. et al *J. Am. Chem. Soc.* 1986, 108, 5908) in 10 mL of ethanol was added 50 mg of 10% Pd/C, and the suspension was hydrogenated at 40 psi for 1.5 h. The reaction was stopped, charged with 60 mg of PtO$_2$, and the hydrogenation was resumed and continued at 45 psi overnight. The reaction mixture was filtered through a pad of silica gel, which was washed with methylene chloride/methanol (100:5). Concentration of the filtrate afforded the corresponding a mixture of 3-amino-7-oxobicyclo[2.2.1]heptane-2-carboxylate methyl esters (ratio 4:3, 0.34 g, 59%). 500 MHz $^1$H NMR (CD$_3$OD) δ Selected peaks for the major isomer: δ4.77 (d, J=6 Hz, 1H), 4.47 (t, J=6 Hz, 1H), 3.76 (s, 3H). Selected peaks for the minor isomer: δ 4.75 (d, J=7 Hz, 1H), 4.35 (t, J=6 Hz, 1H), 3.72 (s, 3H).

MS: m/e 172 [M+H]+

Step B: 3-endo-[N-(N-3,5-Dichlorobenzenesulfonyl)-(L)-prolyl]amino-7-oxobicyclo[2.2.1]heptane-2-carboxulate, methyl ester and 3-exo-[N-(N-3,5-dichlorobenzenesulfonyl)-(L)-prolyl]-amino-7-oxobicyclo[2.2.1]heptane-2-carboxylate, methyl ester To a solution of N-3,5-dichlorobenzenesulfonyl-(L)-proline (0.34, 1.1 mmol) and the mixture of amines obtained from Step A (0.18 g, 1.1 mmol) in 5 mL of methylene chloride at 0° C. was added PyBop (0.62 g, 1.2 mmol) and diisopropylethylamine (0.37 mL, 2.1 mmol). The reaction was stirred at room temperature for 3 h. The reaction mixture was diluted with ethyl acetate (30 mL), and was washed sequentially with saturated $NH_4Cl$, and brine, dried over $Na_2SO_4$ and concentrated. The residue was purified by flash column chromatography on silica gel eluted with 2:1 hexane/ethyl acetate to give 120 mg of a faster eluting component and 120 mg of a slower component plus 180 mg of mixture of the two. Faster eluting component (selected peaks): 500 MHz $^1$H NMR ($CD_3OD$) δ4.73 (t, J=5 Hz, 1H), 4.40–4.35 (m, 1H), 4.34–4.30 (m, 1H), 3.694/3.686 (s, methyl ester of two isomers, 3H), 3.68–3.58 (m, 1H), 3.54–3.46 (m, 1H). Slower eluting component (selected peaks): δ4.71 (d, J=5.5 Hz, 1H), 4.60 (t, J=5.0 Hz), 4.45 (dd, J=8.5, 1.5 Hz), 4.40–4.35 (m, 1H), 3.70 (s, 3H), 3.66–3.60 (m, 1H), 3.52–3.46 (m, 1H).

Step C: 3-endo-[N-(N-3,5-Dichlorobenzenesulfonyl)-(L)-prolyl]amino-7-oxobicyclo[2.2.1]heptane-2-carboxylic acid and 3-exo-[N-(N-3,5-dichlorobenzenesulfonyl)-(L)-prolyl]-amino-7-oxobicyclo[2.2.1]heptane-2-carboxylic acid The two components obtained from Step B were each separately dissolved in 4.5 mL of 1:1:1 methanol/THF/water, and was treated with LiOH hydrate (28 mg), respectively. After stirring at room temperature overnight, the respective reaction mixtures were poured into brine/concentrated HCl (30 mL/1 mL), and the products were extracted with ethyl acetate. The extracts were dried and concentrated, and the residues were purified by flash column chromatography on silica gel eluted with 100:4:1 methanol/methylene chloride/acetic acid to give the endo and exo isomers of 3-[N-(N-3,5-dichlorobenzenesulfonyl)-(L)-prolyl]amino-7-oxobicyclo[2.2.1]heptane-2-carboxylic acid.

First eluted fraction: 500 MHz $^1$H NMR ($CD_3OD$) Selected peaks: d 4.73 (t, J=5 Hz, 1H), 4.42–4.36 (m, 1H), 4.34–4.26 (m, 1H), 3.68–3.58 (m, 1H), 3.56–3.46 (m, 1H).
MS: m/e 480 $(M+NH_4)^+$.

Second eluted fraction: 500 MHz $^1$H NMR ($CD_3OD$) Selected peaks: δ4.74 (t, J=5.0 Hz, 1H), 4.67/4.61 (t, two isomers, J=5.0 Hz), 4.48–4.42 (m, 1H), 3.66–3.60 (m, 1H), 3.54–3.44 (m, 1H).
MS: m/e 480 $(M+NH_4)^+$

EXAMPLE 15

Inhibition of VLA-4 Dependent Adhesion to BSA-CS-1 Conjugate

Step A: Preparation of CS-1 Coated Plates

Untreated 96 well polystyrene flat bottom plates were coated with bovine serum albumin (BSA; 20 μg/ml) for 2 hours at room temperature and washed twice with phosphate buffered saline (PBS). The albumin coating was next derivatized with 10 μg/ml 3-(2-pyridyldithio)propionic acid N-hydroxysuccinimide ester (SPDP), a heterobifunctional crosslinker, for 30 minutes at room temperature and washed twice with PBS. The CS-1 peptide (Cys-Leu-His-Gly-Pro-Glu-Ile-Leu-Asp-Val-Pro-Ser-Thr), which was synthesized by conventional solid phase chemistry and purified by reverse phase HPLC, was next added to the derivatized BSA at a concentration of 2.5 μg/ml and allowed to react for 2 hours at room temperature. The plates were washed twice with PBS and stored at 4° C.

Step B: Preparation of Fluorescently Labeled Jurkat Cells

Jurkat cells, clone E6-1, obtained from the American Type Culture Collection (Rockville, Md.; cat # ATCC TIB-152) were grown and maintained in RPMI-1640 culture medium containing 10% fetal calf serum (FCS), 50 units/ml penicillin, 50 μg/ml streptomycin and 2 mM glutamine. Fluorescence activated cell sorter analysis with specific monoclonal antibodies confirmed that the cells expressed both the α4 and β1 chains of VLA-4. The cells were centrifuged at 400×g for five minutes and washed twice with PBS. The cells were incubated at a concentration of $2 \times 10^6$ cells/ml in PBS containing a 1 μM concentration of a fluorogenic esterase substrate (2',7'-bis-(2-carboxyethyl)-5-(and -6)-carboxyfluorescem, acetoxymethyl ester; BCECF-AM; Molecular Probes Inc., Eugene, Oreg.; catalog #B-1150) for 30–60 minutes at 37° C. in a 5% $CO_2$/air incubator. The fluorescently labeled Jurkat cells were washed two times in PBS and resuspended in RPMI containing 0.25% BSA at a final concentration of $2.0 \times 10^6$ cells/ml.

Step C: Assay Procedure

Compounds of this invention were prepared in DMSO at 100× the desired final assay concentration. Final concentrations were selected from a range between 0.001 nM–100 μM. Three μL of diluted compound, or vehicle alone, were premixed with 300 μL of cell suspension in 96-well polystyrene plates with round bottom wells. 100 μL aliquots of the cell/compound mixture were then transferred in duplicate to CS-1 coated wells. The cells were next incubated for 30 minutes at room temperature. The non-adherent cells were removed by two gentle washings with PBS. The remaining adherent cells were quantitated by reading the plates on a Cytofluor II fluorescence plate reader (Perseptive Biosystems Inc., Framingham, Mass.; excitation and emission filter settings were 485 nm and 530 nm, respectively). Control wells containing vehicle alone were used to determine the level of cell adhesion corresponding to 0% inhibition. Control wells coated with BSA and crosslinker (no CS-1 peptide) were used to determine the level of cell adhesion corresponding to 100% inhibition. Cell adhesion to wells coated with BSA and crosslinker was usually less than 5% of that observed to CS-1 coated wells in the presence of vehicle. Percent inhibition was then calculated for each test well and the $IC_{50}$ was determined from a ten point titration using a validated four parameter fit algorithm.

EXAMPLE 16

Antagonism of VLA-4 Dependent Binding to VCAM-Ig Fusion Protein

Step A: Preparation of VCAM-Ig

The signal peptide as well as domains 1 and 2 of human VCAM (GenBank Accession no. M30257) were amplified by PCR using the human VCAM CDNA (R & D Systems) as template and the following primer sequences: 3'-PCR primer:5'-
AATTATAATTTGATCAACTTACCTGTCAATTCTTTT-ACAGCCTGCC-3';
5'-PCR primer:
5'-ATAGGAATTCCAGCTGCCACCATGCCTGGGAAG-ATGGTCG-3'.

The 5'-PCR primer contained EcoRI and PvuII restriction sites followed by a Kozak consensus sequence (CCACC) proximal to the initiator methionine ATG. The 3'-PCR primer contained a BclI site and a splice donor sequence. PCR was performed for 30 cycles using the following parameters: 1 min. at 94° C., 2 min. at 55° C., and 2 min. at 72° C. The amplified region encoded the following sequence of human VCAM-1:
MPGKMVVILGASNILWIMFAASQAFKIETTPESRYL-AQIGDSVSLTCSTTGCESPFFSWRTQIDSPLNGKV-TNEGTTSTLTMNPVSFGNEHSYLCTATCESRKLEK-GIQVEIYSFPKDPEIHLSGPLEAGKPITVKCSVADV-YPFDRLEIDLLKGDHLMKSQEFLEDADRKSLETK-SLEVTFTPVIEDIGKVLVCRAK- LHIDEMDS-VPTVRQAVKEL. The resulting PCR product of 650 bp was digested with EcoRI and BclI and ligated to expression vector pIg-Tail (R & D Systems, Minneapolis, Minn.) digested with EcoRI and BamHI. The pIg-Tail vector contains the genomic fragment which encodes the hinge region, CH2 and CH3 of human IgG1 (GenBank Accession no. Z17370). The DNA sequence of the resulting VCAM fragment was verified using Sequenase (US Biochemical, Cleveland, Ohio). The fragment encoding the entire VCAM-Ig fusion was subsequently excised from pIg-Tail with EcoRI and NotI and ligated to pCI-neo (Promega, Madison, Wis.) digested with EcoRI and NotI. The resulting vector, designated pCI-neo/VCAM-Ig was transfected into CHO-K1 (ATCC CCL 61) cells using calcium-phosphate DNA precipitation (Specialty Media, Lavalette, N.J.). Stable VCAM-Ig producing clones were selected according to standard protocols using 0.2–0.8 mg/ml active G418 (Gibco, Grand Island, N.Y.), expanded, and cell supernatants were screened for their ability to mediate Jurkat adhesion to wells previously coated with 1.5 µg/ml (total protein) goat anti-human IgG (Sigma, St. Louis, Mo.). A positive CHO-K1/VCAM-Ig clone was subsequently adapted to CHO-SFM serum-free media (Gibco) and maintained under selection for stable expression of VCAM-Ig. VCAM-Ig was purified from crude culture supernatants by affinity chromatography on Protein A/G Sepharose (Pierce, Rockford, Ill.) according to the manufacturer's instructions and desalted into 50 mM sodium phosphate buffer, pH 7.6, by ultrafiltration on a YM-30 membrane (Amicon, Beverly, Mass.).

Step B: Preparation of $^{125}$I-VCAM-Ig

VCAM-Ig was labeled to a specific radioactivity greater that 1000 Ci/mmole with $^{125}$I-Bolton Hunter reagent (New England Nuclear, Boston, Mass.; cat # NEX120-0142) according to the manufacturer's instructions. The labeled protein was separated from unincorporated isotope by means of a calibrated HPLC gel filtration column (G2000SW; 7.5×600 mm; Tosoh, Japan) using uv and radiometric detection.

Step C: VCAM-Ig Binding Assay

Compounds of this invention were prepared in DMSO at 100× the desired final assay concentration. Final concentrations were selected from a range between 0.001 nM–100 µM. Jurkat cells were centrifuged at 400×g for five minutes and resuspended in binding buffer (25 mM HEPES, 150 mM NaCl, 3 mM KCl, 2 mM glucose, 0.1% bovine serum albumin, pH 7.4). The cells were centrifuged again and resuspended in binding buffer supplemented with $MnCl_2$ at a final concentration of 1 mM. Compounds were assayed in Millipore MHVB multiscreen plates (cat# MHVBN4550, Millipore Corp., Massachusetts) by making the following additions to duplicate wells: (i) 200 µL of binding buffer containing 1 mM $MnCl_2$; (ii) 20 µL of $^{125}$I-VCAM-Ig in binding buffer containing 1 mM $MnCl_2$ (final assay concentration –100 pM); (iii) 2.5 µL of compound solution or DMSO; (iv) and 0.5×10$^6$ cells in a volume of 30 µL. The plates were incubated at room temperature for 30 minutes, filtered on a vacuum box, and washed on the same apparatus by the addition of 100 µL of binding buffer containing 1 mM $MnCl_2$. After insertion of the multiscreen plates into adapter plates (Packard, Meriden, Conn., cat# 6005178), 100 µL of Microscint-20 (Packard cat#6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Control wells in which cells were omitted were used to determine the level of binding corresponding to 100% inhibition. Binding of $^{125}$I-VCAM-Ig in the absence of cells was usually less than 5% of that observed using cells in the presence of vehicle. Percent inhibition was then calculated for each test well and the $IC_{50}$ was determined from a ten point titration using a validated four parameter fit algorithm.

EXAMPLE 17

Antagonism of $\alpha_4\beta_7$ Dependent Binding to VCAM-Ig Fusion Protein

Step A: $\alpha_4\beta_7$ Cell line

RPMI-8866 cells (a human B cell line $\alpha_4^+\beta_1^-\beta_7^+$; a gift from Prof. John Wilkins, University of Manitoba, Canada) were grown in RPMI/10% fetal calf serum/100 U penicillin/100 µg streptomycin/2 mM L-glutamine at 37° C., 5% carbon dioxide. The cells were pelleted at 1000 rpm for 5 minutes and then washed twice and resuspended in binding buffer (25 mM HEPES, 150 mM NaCl, 0.1% BSA, 3 mM KCl, 2 mM Glucose, pH 7.4).

Step B: VCAM-Ig Binding Assay

Compounds of this invention were prepared in DMSO at 100× the desired final assay concentration. Final concentrations were selected from a range between 0.001 nM–100 µM. Compounds were assayed in Millipore MHVB multiscreen plates (Cat# MHVBN4550) by making the following sequential additions to duplicate wells: (i) 100 µl/well of binding buffer containing 1.5 mM $MnCl_2$; (ii) 10 µl/well $^{125}$I-VCAM-Ig in binding buffer (final assay concentration <500 pM); (iii) 1.5 µl/well test compound or DMSO alone; (iv) 38 µl/well RPMI-8866 cell suspension (1.25×10$^6$ cells/well). The plates were incubated at room temperature for 45 minutes on a plate shaker at 200 rpm, filtered on a vacuum box, and washed on the same apparatus by the addition of 100 µL of binding buffer containing 1 mM $MnCl_2$. After insertion of the multiscreen plates into adapter plates (Packard, Meriden, Conn., cat#6005178), 100 µL of Microscint-20 (Packard cat#6013621) was added to each well. The plates were then sealed, placed on a shaker for 30 seconds, and counted on a Topcount microplate scintillation counter (Packard). Control wells containing DMSO alone were used to determine the level of VCAM-Ig binding corresponding to 0% inhibition. Wells in which cells were omitted were used to determine the level of binding corresponding to 100% inhibition. Percent inhibition was then calculated for each test well and the $IC_{50}$ was determined from a ten point titration using a validated four parameter fit algorithm.

What is claimed is:

1. A compound of the formula I:

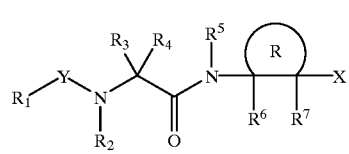

I or a pharmaceutically acceptable salt thereof wherein:
X is —C(O)OR$^d$;
Y is —S(O)$_2$—;

R is a saturated or partially saturated monocyclic or bicyclic ring having 0 heteroatoms, optionally benzo-fused and optionally substituted with from 1–4 groups selected from $R^b$;

$R^1$ is Cy optionally substituted with one to four substituents independently selected from $R^b$;

$R^2$ and $R^3$ are each hydrogen, or $R^2$ and $R^3$ together with the atoms to which they are attached form a pyrrolidine ring, wherein said ring may be isolated or benzo-fused, and optionally substituted with one to four substituents independently selected from $R^b$;

$R^4$ is
1) hydrogen,
2) $C_{1-10}$alkyl,
3) $C_{2-10}$alkenyl,
4) $C_{2-10}$alkynyl,
5) aryl, or
6) aryl $C_{1-10}$alkyl, wherein alkyl, alkenyl and alkynyl are optionally substituted with one to four substituents independently selected from $R^a$, and aryl is optionally substituted with one to four substituents independently selected from $R^b$; or $R^3$, $R^4$ and the carbon to which they are attached form a 3–7 membered carbocyclic ring;

$R^5$ is
1) hydrogen,
2) $C_{1-10}$ alkyl,
3) Cy, or
4) Cy-$C_{1-10}$ alkyl, wherein alkyl is optionally substituted with one to four substituents independently selected from $R^a$; and Cy is optionally substituted with one to four substituents independently selected from $R^b$;

$R^6$ is selected from the group consisting of:
1) hydrogen,
2) $C_{1-10}$alkyl,
3) $C_{2-10}$alkenyl,
4) $C_{2-10}$alkynyl,
5) Cy-$(Cy^1)_p$,
6) Cy-$(Cy^1)_p$-$C_{1-10}$alkyl,
7) Cy-$(Cy^1)_p$-$C_{2-10}$alkenyl,
8) Cy-$(Cy^1)_p$-$C_{2-10}$alkynyl, alkyl, alkenyl and alkynyl are optionally substituted with one to four substituents independently selected from $R^a$; and Cy and $Cy^1$ are optionally substituted with one to four substituents independently selected from $R^b$; or $R^6$ together with the carbon atom to which it is attached and another carbon atom of R form a carbocyclic ring having from 5–8 members optionally substituted with $R^b$;

$R^7$ is
1) hydrogen
2) $C_{1-10}$alkyl,
3) $C_{2-10}$alkenyl,
4) $C_{2-10}$alkynyl,
5) Cy,
6) Cy-$C_{1-10}$alkyl,
7) Cy-$C_{2-10}$alkenyl,
8) Cy-$C_{2-10}$alkynyl,
9) $C_{1-10}$alkoxy,
10) Cy-O,
11) Cy-$C_{1-10}$alkoxy,
12) —S(O)$_m$R$^d$,
13) —SR$^d$,
14) —S(O)$_2$OR$^d$,
15) —S(O)$_m$NR$^d$R$^e$,
16) hydroxy,
17) —NR$^d$R$^e$,
18) —O(CR$^f$R$^g$)$_n$NR$^d$R$^e$,
19) —OC(O)R$^d$,
20) —CN,
21) —C(O)NR$^d$R$^e$,
22) —NR$^d$C(O)R$^e$,
23) —OC(O)NR$^d$R$^e$,
24) —NR$^d$C(O)OR$^e$, or
25) —NR$^d$C(O)NR$^d$R$^e$, wherein alkyl, alkenyl and alkynyl are optionally substituted with one to four substituents selected from $R^a$, and Cy is optionally substituted with one to four substituents independently selected from $R^b$; or $R^7$ together with the carbon atom to which it is attached and another carbon atom of R form a carbocyclic ring having from 5–8 members optionally substituted with $R^b$; or $R^6$ and $R^7$ together represents a double bond between the carbon atoms to which they are attached;

$R^a$ is
1) —CF$_3$;
2) —OR$^d$,
3) —NO$_2$,
4) halogen
5) —S(O)$_m$R$^d$,
6) —SR$^d$,
7) —S(O)$_2$OR$^d$,
8) —S(O)$_m$NR$^d$R$^e$,
9) —NR$^d$R$^e$,
10) —O(CR$^f$R$^g$)$_n$NR$^d$R$^e$,
11) —C(O)R$^d$,
12) —CO$_2$R$^d$,
13) —CO$_2$(CR$^f$R$^g$)$_n$CONR$^d$R$^e$,
14) —OC(O)R$^d$,
15) —CN,
16) —C(O)NR$^d$R$^e$,
17) —NR$^d$C(O)R$^e$,
18) —OC(O)NR$^d$R$^e$,
19) —NR$^d$C(O)OR$^e$, or
20) —NR$^d$C(O)NR$^d$R$^e$;
21) —CR$^d$(N—OR$^e$), or
22) Cy optionally substituted with a group independently selected from $R^c$;

$R^b$ is
1) a group selected from $R^a$,
2) $C_{1-10}$ alkyl,
3) $C_{2-10}$ alkenyl,
4) $C_{2-10}$ alkynyl, or
5) Cy-$C_{1-10}$ alkyl, wherein alkyl, alkenyl, alkynyl, and Cy are optionally substituted with a group independently selected from $R^c$;

$R^c$ is
1) halogen,
2) amino,
3) carboxy,
4) $C_{1-4}$alkyl,
5) $C_{1-4}$alkoxy,
6) aryl,
7) aryl $C_{1-4}$alkyl, or
8) aryloxy;

$R^d$ and $R^e$ are independently selected from hydrogen, $C_{1-10}$alkyl, $C_{2-10}$alkenyl, $C_{2-10}$alkynyl, Cy and Cy-$C_{1-10}$alkyl, wherein alkyl, alkenyl, alkynyl and Cy is optionally substituted with one to four substituents independently selected from $R^c$;

$R^f$ and $R^g$ are independently selected from hydrogen, $C_{1-10}$alkyl, Cy and Cy-$C_{1-10}$alkyl;
m is 0, 1 or 2;
n is an integer from 1 to 10;
p is 0 or 1.

2. A compound of claim 1 wherein $R^2$, $R^3$ and the atoms to which they are attached together form pyrrolidine optionally substituted with from one to four groups selected from $R^b$.

3. A compound of claim 1 wherein $R^1$ is aryl optionally substituted with one or two groups selected from $R^b$.

4. A compound of claim 1 wherein R, R6 and R7 together represent the following, and N and X are shown as necessary:

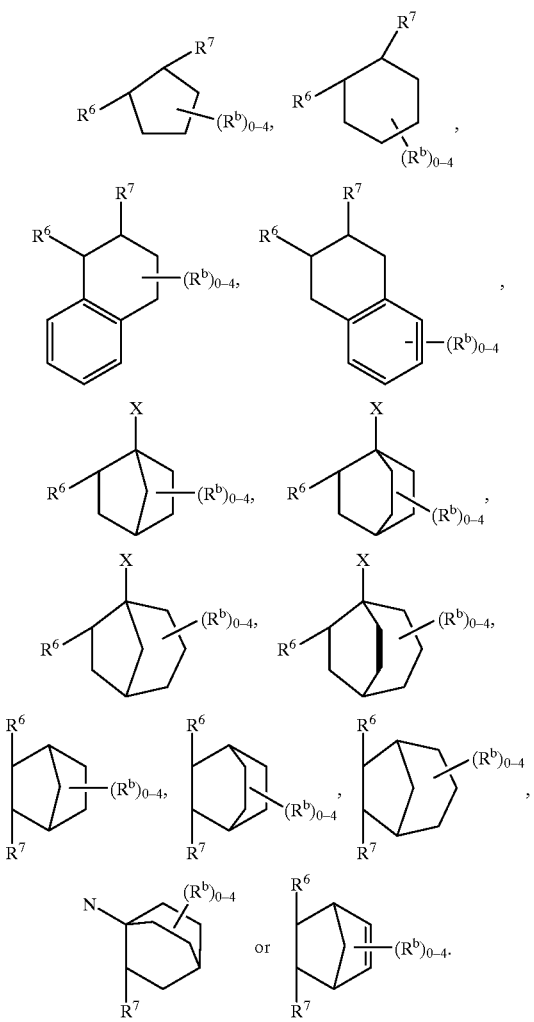

5. A compound of claim 1 selected from the group consisting of:
3-exo-[N-(N-3,5-dichlorobenzenesulfonyl)-(L)-prolyl] aminobicyclo[2.2.1]-heptane-2-carboxylic acid;
cis-2-[N-(N-3,5-dichlorobenzenesulfonyl)-(L)-prolyl] amino-1-cyclohexanecarboxylic acid;
trans-2-[N-(N-3,5-dichlorobenzenesulfonyl)-(L)-prolyl] amino-1-cyclohexanecarboxylic acid;
cis-2-[N-(N-3,5-dichlorobenzenesulfonyl)-(L)-prolyl] amino-1-cyclopentanecarboxylic acid;
2-[N-(N-3,5-dichlorobenzenesulfonyl)-(L)-prolyl]amino-1-cyclopentene-1-carboxylic acid;
3-endo-[N-(N-3,5-dichlorobenzenesulfonyl)-(L)-prolyl] aminobicyclo[2.2.1]-hept-5-ene-2-carboxylic acid;
3-endo-[N-(N-3,5-dichlorobenzenesulfonyl)-(L)-prolyl] aminobicyclo[2.2.1]-heptane-2-carboxylic acid;
trans-2-[N-(N-3,5-dichlorobenzenesulfonyl-N-methyl)-(L)-valyl]amino-1-cyclohexanecarboxylic acid;
trans-2-[N-(N-cyclohexyl-N-3,5-dichlorobenzenesulfonyl) glycyl]amino-1-cyclohexanecarboxylic acid;
trans-2-[N-(N-3,5-dichlorobenzenesulfonyl-N-methyl)-(L)-phenylalanyl]amino-1-cyclohexanecarboxylic acid; and
trans-2-[N-(N-3,5-dichlorobenzenesulfonyl)-(L)-phenylalanyl]amino-1-cyclohexanecarboxylic acid;
3-endo-[N-(N-3,5-dichlorobenzenesulfonyl)-(L)-prolyl] aminobicyclo[2.2.2]-octane-2-carboxylic acid;
3-endo-N-(N-3,5-dichlorobenzenesulfonyl)-(L)-2(S)-methyl-prolyl]aminobicyclo[2.2.1]-heptane-2-carboxylic acid.

6. A method for inhibiting cell adhesion in a mammal which comprises administering to said mammal an effective amount of a compound of claim 1.

7. A method for the treatment of diseases, disorders, conditions or symptoms mediated by cell adhesion in a mammal which comprises administering to said mammal an effective amount of a compound of claim 1.

8. A method for the treatment of asthma in a mammal which comprises administering to said mammal a therapeutically effective amount of a compound of claim 1.

9. A method for the treatment of allergic rhinitis in a mammal which comprises administering to said mammal a therapeutically effective amount of a compound of claim 1.

10. A method for the treatment of multiple sclerosis in a mammal which comprises administering to said mammal a therapeutically effective amount of a compound of claim 1.

11. A method for the treatment of atherosclerosis in a mammal which comprises administering to said mammal a therapeutically effective amount of a compound of claim 1.

12. A method for the treatment of inflammation in a mammal which comprises administering to said mammal an effective amount of a compound of claim 1.

13. A method for the treatment of inflammatory bowel disease in a mammal which comprises administering to said mammal a therapeutically effective amount of a compound of claim 1.

14. A pharmaceutical composition which comprises a compound of claim 1 and a pharmaceutically acceptable carrier thereof.

* * * * *